US006465487B1

(12) United States Patent
Block et al.

(10) Patent No.: US 6,465,487 B1
(45) Date of Patent: Oct. 15, 2002

(54) INHIBITION OF MEMBRANE-ASSOCIATED VIRAL REPLICATION

(75) Inventors: Timothy M. Block, Doylestown, PA (US); Raymond A. Dwek, North Hinskey (GB); Baruch S. Blumberg, Philadelphia, PA (US); Anand Mehta, Landenberg, PA (US); Frances Platt, Long Hanborough (GB); Terry D. Butters, Garsington (GB); Nicole Zitzmann, Odendorf (DE)

(73) Assignees: Synergy Pharmaceuticals, Inc., Somerset, NJ (US); Thomas Jefferson University, Philadelphia, PA (US); The Chancellor, Masters and Scholars of the University of Oxford, Oxford (GB)

( * ) Notice: Subject to any disclaimer, the term of this patent is extended or adjusted under 35 U.S.C. 154(b) by 0 days.

(21) Appl. No.: 09/209,033

(22) Filed: Dec. 10, 1998

Related U.S. Application Data

(60) Provisional application No. 60/069,245, filed on Dec. 11, 1997.

(51) Int. Cl.$^7$ ............................................. A61K 31/445
(52) U.S. Cl. ....................... 514/315; 514/317; 514/326; 514/327; 514/328
(58) Field of Search ................................ 514/315, 317, 514/326, 327, 328

(56) References Cited

U.S. PATENT DOCUMENTS

| | | |
|---|---|---|
| 4,246,345 A | 1/1981 | Kinast et al. |
| 4,266,025 A | 5/1981 | Kinast et al. |
| 4,405,715 A | 9/1983 | Kinast et al. |
| 4,806,650 A | 2/1989 | Schröder et al. |
| 5,043,273 A | 8/1991 | Scudder et al. |
| 5,091,418 A | 2/1992 | Sawada et al. |
| 5,103,008 A | 4/1992 | Scudder et al. |
| 5,264,356 A | 11/1993 | Rohrschneider |
| 5,310,745 A | 5/1994 | Partis et al. ................. 514/315 |
| 5,538,865 A | 7/1996 | Reyes et al. |
| 5,622,972 A | 4/1997 | Bryant et al. |
| 5,643,888 A | 7/1997 | Rohrschneider |
| 5,801,185 A | 9/1998 | Platt et al. |

FOREIGN PATENT DOCUMENTS

| | | |
|---|---|---|
| EP | 0 367 747 | 5/1990 |
| EP | 0 445 098 | 9/1991 |
| WO | WO 98/35685 | 8/1998 |
| WO | WO 98/35685 | 9/1998 |
| WO | WO 99/24401 | 5/1999 |
| WO | WO 01/10429 | 2/2001 |

OTHER PUBLICATIONS

Schlesinger et al 102CA:197584, 1985.*
Courageot et al., $_\alpha$–Glucosidase inhibitors reduce dengue virus production by affecting the initial steps of virion morphogenesis in the endoplasmic reticulum, Journal of Virology, 2000, 74:564–572.

McDowell et al., Glucose Trimming and Mannose Trimming Affect Different Phases of the Maturation of Sindbis Virus in Infected BHK Cells, Academic Pres. Inc., 1987, 161:37–44.

Schlesinger et al., The effects of inhibitors of glucosidase I on the formation of Sindbis virus, Virus Research, 1985, 2:139–149.

Schlesinger et al., Togaviridae: The viruses and their replication, Fields Virology, $3^{rd}$ Ed. (Fields et al.), 1996, pp. 825 and 850–851.

Winchester et al., Amino–sugar glycosidase inhibitors: Versatile tools for glycobiologists, Glycobiology, 1992, 2:199–210.

Zitzmann et al., Imino sugars inhibit the formation and secretion of bovine viral diarrhea virus, a pestivirus model of hepatitis C virus: Implications for the development of broad spectrum anti–hepatitus virus agents, Proc. Natl. Acad. Sci. USA, 1999, 96: 11878–11882.

Acosta, E. et al. Agents for treating human immunodeficiency virus infection. Am J Hosp Pharm 51:2251–2267 (1994).

Andersen, S. et al. Synthesis and glucosidase inhibitory activities of deoxyfluoro derivatives of the powerful glucosidase inhibitors 1–deoxynojirimycin and 2,5–didexy–2, 5–imino–D–mannitol, Institute of Organic Chemistry, Technical University Graz. http://www–orgc.tu–graz.ac.at/ectoc/am2.html 1–10 (1998).

Berge, S. et al. Pharmaceutical salts. J Pharm Sci 66(1):1–18 (1977).

Block T. et al. Secretion of human hepatitis B virus is inhibited by the imino sugar N–butyldeoxynojirimycin. Proc Natl Acad Sci USA 91:2235–2239 (1994).

Block, T. et al. Treatment of chronic hepadnavirus infection in a woodchuck animal model with an inhibitor of protein folding and trafficking. Nat Med 4(5):610–614 (1998).

Chelbi–Alix, M. et al. Ethanol induces 2',5'–oligoadenylate synthetase and antiviral activities through interferon–β production. J Biol Chem 267(3):1741–1745 (1992).

Cobbold C. et al. Involvement of the endoplasmic reticulum in the assembly and envelopment of african swine fever virus. J Virol 70(12):8382–8390 (1996).

Dedera, D. et al. Attenuation of HIV–1 infectivity by an inhibitor of oligosaccharaide processing. AIDS Res Hum Retroviruses 6:785–794 (1990).

Donis R. Molecular biology of bovine viral diarrhea virus and its interactions with the host. Vet Clin Am 11(3):393–423 (1995).

(List continued on next page.)

Primary Examiner—Russell Travers
(74) Attorney, Agent, or Firm—Pillsbury Winthrop LLP

(57) ABSTRACT

Methods for inhibiting morphogenesis of host cell membrane-budding viruses and infections caused thereby using compounds that inhibit host cell glucosidase or glucosyltransferase enzymes. Methods for treating lipid storage diseases using compounds that inhibit glucosyl transferance enzymes.

38 Claims, 9 Drawing Sheets

OTHER PUBLICATIONS

Elbein, A. Inhibitors of the biosynthesis and processing of N–linked oliosaccharide chains. Ann Rev Biochem 56:497–534 (1987).

Fischer, P. et al. The α–glucosidase inhibitor N–butyldeoxynojirimycin inhibits human immunodeficiency virus entry at the level of post–CD4 binding. J Virol 69(9):5791–5797 (1995).

Fischer, P. et al. N–butyldeoxynojirimycin–mediated inhibition of human immunodeficiency virus entry correlates with impaired gp 120 shedding and gp41 exposure. J Virol Fischer, P. et al. N–butyldeoxynojirimycin–mediated inhibition of human immunodeficiency virus entry correlates with changes in antibody recognition of the V1/V2 region of gp120. J Virl 70(10):7143–7152 (1996).

Fourel, I. et al. The carbocyclic analogy of 2'–deoxyguanosine induces a prolonged inhibition of duck, hepatitis B virus DNA synthesis in primary hepatocyte cultures and in the liver. J Virol 68:1059–1065 (1994).

Guidotti, L. et al. Interleukin–2 and alpha/beta interferon down–regulate hepatitis B virus gene expression in vivo by tumor necrosis factor–dependent and –independent pathways. J Virol 68(3):1265–1270 (1994).

Harasawa, R. et al. Demonstration and genotyping of pestivirus RNA from mammalian cell lines. Micro Immunol 39:979–985 (1995).

Henzler, H. et al. Avoiding viral contamination in biotechnological and pharmaceutical processes. Nat Biotechnol 16:1077–1078 (1998).

Hoofnagle, J. et al. The treatment of chronic viral hepatitis. New Eng J Med 336(5):347–356 (1997).

Huovila, A. et al. Hepatitis B surface antigen assembles in a post–ER pre–golgi compartment. J Cell Biol 118(6):1305–1320 (1992).

Lu, X. et al. Evidence that N–linked glycosylation is necesary for hepatitis B virus secretion. Virology 213:001–006 (1995).

Lu, X. et al. Aberrant trafficking of hepatitis B virus glycoproteins in cells in which N–glycan processing is inhibited. Proc Nat Acad Sci USA 94:2380–2385 (1997).

Martin, J. et al. Pilot study of recombinant human granulocyte–macrophage colony–stimulating factor in the treatment of chronic hepatitis B. Hepatology 18:775–780 (1993).

Mehta, A. et al. Hepatitis B virus (HBV) envelope glycoproteins vary drastically in their sensitivity to glycan processing: evidence that alteration of a single N–linked glycosylation site can regulate HBV secretion, Proc natl Acad Sci USA. 94:1822–1827 (1997).

Miller, R. et al. Hepatitis C virus shares amino acid sequence similarity with pestiviruses and flavivurses as well as members of two plant virus supergroups. Proc Natl Acad Sci USA.

Patzer, E. et al. Intracellular assembly and packaging of hepatitis B surface antigen particles occur in the endopasmic reticulum. J Virol 58(3) 884–892 (1986).

Platt, F. et al. Prevention of lysosomal storage in tay–sachs mice treated with N–butyldeoxynojirimycin. Science 276:428–431 (1997).

Platt, F. et al. N–Butyldeoxynojirimycin is a novel inhibitor of glycolipid biosynthesis. J Biol Chem 269(11):8362–8365 (1994).

Platt, F. et al. N–Butyldeoxygalactonojirimycin inhibits glycolipid biosynthesis but does not affect N–Linked oligosaccharide processing. J Biol Chem 269(43):27108–27114 (1994).

Saunier, B. et al. Inhibition of N–linked complex oligosaccharide formation by 1–deoxynojirimycin, an inhibitor of processing glucosidases. J Biol Chem 257:14155–14161 (1982).

Sullivan, D. et al. A nested polymerase chain reaction assay to differentiate pestiviruses, Virus Res 38:231–239 (1995).

Suzich, J. et al. Hepatitis C virus NS3 protein polynucleotide–stimulated nucleoside triphosphatase and comparison with the related pestivirus and flavivirus enzymes. J Virol 67:6152–6158 (1993).

Taylor, D. et al. Inhibition of α–glucosidase I of the glycoprotein–processing enzymes by 6–O–butanoyl castanospermine (MDL 28,574) and its consequences in human immunodeficiency virus–infected T cells, Antimicrob Agents Chemother 38(8):1780–1787 (1994).

Hepatitis C Treatment. The Washington Post. Nov. 11, 1997; Sect. A2.

van den Broek et al., "Chemical modification of azasugars, inhibitors of N–glycoprotein–processing glycosidasea and of HIV–I infection," Recl. Trav. Chim. Pays–Bas 112, 1993, pp. 82–94.

van den Broek et al., "Synthesis of oxygen–substituted N–alkyl 1–deoxynojirimycin derivatives: aza sugar α–glucosidase inhibitors showing antiviral (HIV–1) and immunosuppressive activity," Recl. Trav. Chem. Pays–Bas 113, 1994, pp. 507–516.

Esposito et al., "Synthesis of Amphiphilic Polyhydroxylated Pyrrolidines as Potential Glycosidase Inhibitors," Tetrahedron Letters 39, 1998, pp. 6543–6546.

* cited by examiner

FIGURE 2A

A    BVDV secretion in the presence of N-butyl-DNJ

B    BVDV secretion in the presence of N-nonyl-DNJ

IC50 = 2.5 uM = 0.65 ug/ml

Effect of DMJ on BVDV plaque formation

FIGURE 4

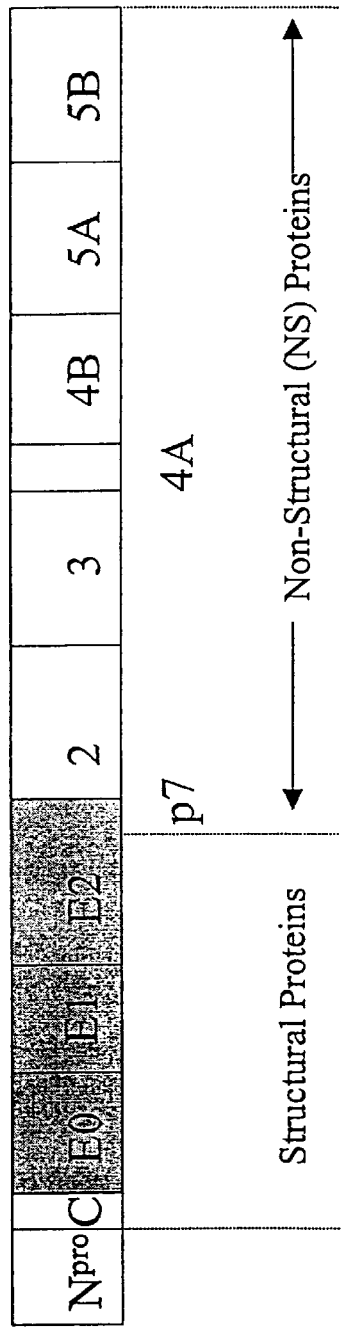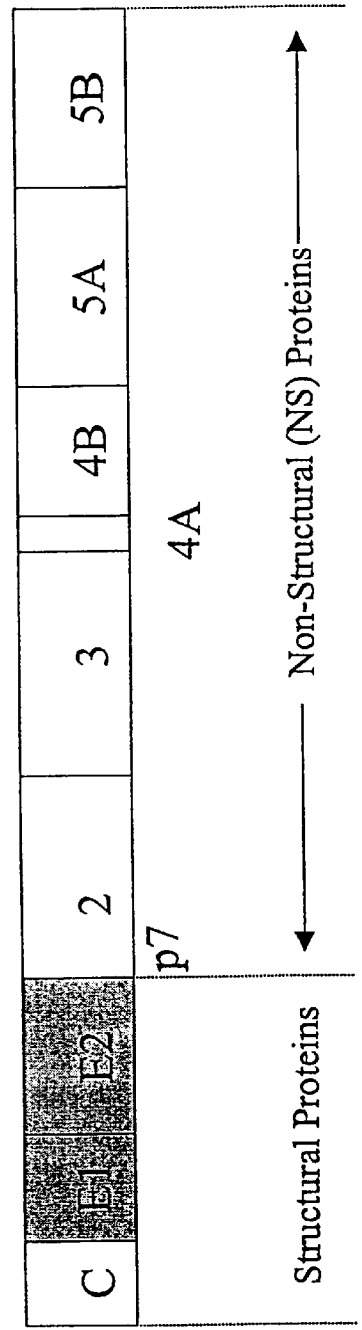
FIGURE 9A
FIGURE 9B

INHIBITION OF MEMBRANE-ASSOCIATED VIRAL REPLICATION

This application claims the benefit of priority of U.S. Provisional Application Serial No. 60/069,245, filed Dec. 11, 1997.

FIELD OF THE INVENTION

The invention relates to the treatment of viral infections with compounds that inhibit glucosidase activity in the host cell. It relates as well to the treatment of lipid storage disease with compounds that inhibit glucosyltransferase activity in the affected cells. It relates particularly to the use of 1,5-dideoxy-1,5-imino-D-glucitol and derivatives thereof.

BACKGROUND OF THE INVENTION

More than 40 million people worldwide are chronically infected with the hepatitis C virus (HCV), and this represents one of the most serious threats to the public health of developed nations (Hoofnagle et al. (1997) New Engl J Med 336:347–356). Hepatitis C infection is the cause of more than 10,000 deaths annually in the United States (Hepatitis C Treatment, Washington Post, Nov. 11, 1997, at A2), a number that is expected to triple in the next twenty years in the absence of effective intervention. Chronic HCV also increases the risk of liver cancer. There are more than 40 million people worldwide who are chronically infected with HCV, representing one of the most serious threats to the public health of developed nations (Hoofnagle et al. (1997) New Engl J Med 336:347–356). Persistent infection develops in as many as 85% of HCV patients and in at least 20% of these patients the chronic infection leads to cirrhosis within twenty years of onset of infection. With an estimated 3.9 million North Americans chronically infected, complications from Hepatitis C infection is now the leading reason for liver transplantation in the United States.

HCV is an RNA virus belonging to the Flaviviridae family. Individual isolates consist of closely related, yet heterologous populations of viral genomes. This genetic diversity enables the virus to escape the host's immune system, leading to a high rate of chronic infection.

Therapeutic interventions which are effective for treatment of HCV infection are limited in number and effectiveness. Standard treatment for HCV infection includes administration of interferon-alpha. However, interferon-alpha is of limited use in about 20% of the HCV-infected population (Hoofnagle et al. (1997) New Engl J Med 336:347–356) and treatment with this compound results in long-term improvement in only 5% of patients. Furthermore, the complications and limitations of interferon-alpha seriously limit the applicability of the treatment. An experimental treatment comprising administration of interferon-alpha and ribavirin (1-α-D-ribofuranosyl-1 H-1,2,4-triazole-3-carboxamide) resulted in long-term improvement in only half of patients suffering a relapse of HCV infection (Hepatitis C Treatment Washington Post, Nov. 11, 1997, at A2). Clearly, the disappointing results with interferon must prompt a search for more effective and less toxic therapeutics. Thus, a critical need remains for a therapeutic intervention that effectively treats HCV infection.

In addition to those people chronically infected with HCV, there are more than 350 million people chronically infected with HBV. More than 150 million of these people are likely to die from liver disease in the absence of intervention. As many as 20 million HBV carriers reside in developed nations, as do most HCV carriers.

A large number of individuals who are infected with HCV are also infected with HBV. The therapy for combined HBV/HCV infection is particularly challenging because the HBV and HCV viruses differ from one another in therapeutically significant ways. HBV is a hepadnavirus, while HCV is a pestivirus. HBV is a DNA-containing virus, the genome of which is replicated in the nucleus of the infected cell using a combination of a DNA-dependent RNA polymerase and an RNA-dependent DNA polymerase (i.e., a reverse transcriptase). HCV is an RNA-containing virus, the genome of which is replicated in the cytoplasm of the infected cell using one or more types of RNA-dependent RNA polymerases. Despite the frequent concurrence of HBV infection and HCV infection, a number of compounds known to be effective for treating HBV infection are not effective against HCV. For example, lamivudine (the nucleoside analog 3TC) is useful for treating HBV infection, but is not useful for treating HCV infection. The difference in the susceptibility of HBV and HCV to antiviral agents no doubt relates to their genetically based replicative differences. There remains a particularly critical need for a therapeutic intervention that effectively treats both HBV and HCV infection.

Animal viruses that acquire their envelope from a membrane associated with the intracellular membrane of an infected animal cell cause significant losses to the livestock industry (Sullivan et al. (1995) Virus Res 38:231–239). Such animal viruses include pestiviruses and flaviviruses such as bovine viral diarrhea virus (BVDV), classical swine fever virus, border disease virus and hog cholera virus.

The flavivirus group to which HCV belongs is known to include the causative agents of numerous human diseases transmitted by arthropod vectors. Human diseases caused by flaviviruses include various hemorrhagic fevers, hepatitis, and encephalitis. Viruses known to cause these diseases in humans have been identified and include, for example, yellow fever virus, dengue viruses 1-4, Japanese encephalitis virus, Murray Valley encephalitis virus, Rocio virus, West Nile fever virus, St. Louis encephalitis virus, tick-borne encephalitis virus, Louping ill virus, Powassan virus, Omsk hemorrhagic fever virus, and Kyasanur forest disease virus. A critical need therefore also exists for treating animals, as well as humans, infected with a flavivirus or a pestivirus.

SUMMARY OF THE INVENTION

The invention provides a method of inhibiting morphogenesis of a virus which acquires its envelope from a membrane-associated with the intracellular membrane of an infected cell, the method comprising administering to the cell a glucosidase inhibitor in an amount effective to inhibit the activity of a glucosidase enzyme associated with the endoplasmic reticulum of the cell. In one aspect, the virus is selected from the group consisting of a flavivirus and a pestivirus, such as a Hepatitis C virus, a bovine viral diarrhea virus, a classical swine fever virus, a border disease virus, or a hog cholera virus. In another aspect, the membrane is selected from the group consisting of a membrane that surrounds the lumen of the endoplasmic reticulum and a membrane that surrounds a lumen of the Golgi apparatus.

In a preferred embodiment of the invention, the glucosidase inhibitor is 1,5-dideoxy-1,5-imino-D-glucitol or a derivative thereof selected from the group consisting of an N-alkyl, N-acyl, N-aroyl, N-aralkyl, and O-acyl derivatives.

The invention includes a method of inhibiting morphogenesis of a virus that acquires its envelope from an internal cell membrane associated with the endoplasmic reticulum (ER). The method comprises administering a glucosidase inhibitor to the cell in an amount effective to inhibit the activity of a glucosidase enzyme associated with the endoplasmic reticulum of the cell, thereby inhibiting morphogenesis of the virus. Mammalian cells infected with the subject viruses including, but not limited to, human liver cells and bovine monocytes are particularly contemplated as therapeutic targets.

The invention also includes a method of treating an animal infected with a virus that is characterized by acquiring its envelope from a membrane associated with the ER of a virus-infected cell. The method comprises administering a glucosidase inhibitor to the animal in an amount effective to inhibit the activity of a glucosidase enzyme with the endoplasmic reticulum of a virus-infected cell of the animal, thereby reducing, ablating, or diminishing the virus infection in the animal. The animal is preferably a mammal such as a pig or a cow and, particularly, a human being.

The methods of the invention are useful for inhibiting morphogenesis of a virus, or for treating an animal infected with any virus that acquires its envelope from a membrane associated with the ER. Because both flaviviruses and pestiviruses acquire their envelopes from membranes associated with the ER, the methods of the invention are contemplated to be particularly useful for inhibiting morphogenesis of, or for treatment of infection by flaviviruses and pestiviruses. Infections by flaviviruses include, but are not limited to, those caused by yellow fever virus, dengue viruses 1-4, Japanese encephalitis virus, Murray Valley encephalitis virus, Rocio virus, West Nile fever virus, St. Louis encephalitis virus, tick-borne encephalitis virus, Louping ill virus, Powassan virus, Omsk hemorrhagic fever virus, and Kyasanur forest disease virus. Infections by pestiviruses include, but are not limited to, those caused by HCV, rubella virus, BVDV, classical swine fever virus, border disease virus, and hog cholera virus.

According to yet another aspect of the invention, there is provided a method for targeting a glucosidase inhibitor or glucosyltransferase inhibitor to the liver cell of an animal by targeting said liver cells with an N-alkyl derivative of a 1,5-dideoxy-1,5imino-D-glucitol. In a preferred embodiment the derivative is an N-nonyl-1,5-dideoxy-1,5-imino-D-glucitol.

According to another aspect of the invention there is provided a method for treating lipid storage disease, where a glucosyl- or galactosyl-linked lipid accumulates in the cells of the affected individual. In one embodiment of this aspect of the invention the method comprises treating a lysosomal storage disease in an animal by administering an effective glucosyltransferase-inhibiting amount of an N-nonyl-1,5-dideoxy-1,5-imino-D-glucitol derivative to the affected cells of said animal, whereby the production of glycolipids in said cells is limited. In a preferred embodiment of this aspect of the invention, the animal is affected with Tay-Sachs, Gaucher's. Krabbe's or Fabry's disease.

According to yet another aspect of the invention there is provided a prophylactic method for protecting a mammal infected by a virus that acquires a viral component from an internal membrane of an animal cells from developing a cancer that is among the sequelae of infection by said virus, comprising administering to the virus infected cell of the animal an effective anti-viral amount of an animal cell glucosidase-inhibitor. In a preferred embodiment of this aspect of the invention the antiviral glucosidase inhibitor is selected from the group consisting of 1,5-dideoxy-1,5-imino-D-glucitol and derivatives thereof.

BRIEF DESCRIPTION OF THE DRAWINGS

FIG. 2 shows the secretion of infectious BVDV in cultures of infected MDBK cells treated with DNJ derivatives. The Y axis scale represents the number of plaques observed in the treated systems as a percentage of the plaques resulting from infection with an inhibitor-free supernate. The X axis scale represents the inhibitor concentrations used in the plaque assays. The IC50 is indicated at the bottom of the graphs. FIG. 2a: inhibition by N-butyl-DNJ; and FIG. 2b: inhibition by N-nonyl-DNJ.

FIG. 4 shows the effect of increasing concentrations of deoxymannojirimycin (DMJ) on BVDV plaque formation in cultures of infected cells, up to a concentration that protects treated cells from the lethal effects of ECA, a complex sugar-binding lectin. The Y axis scale represents the number of plaques in the treated system as a percentage of the plaques resulting from infection with inhibitor-free plaque assay supernate (Y=100%). The X axis indicates inhibitor concentrations used in the assays.

(FIG. 5b) non-treated BVDV-infected cells; and (FIG. 5C) N-butyl-DNJ treated BVDV-infected cells.

FIG. 9 shows the organization of the polyprotein sequence of representative Flaviviridae viruses: (a) the sequence associated with the pestivirus BVDV; and (b) the sequence associated with hepatitis C virus.

DETAILED DESCRIPTION OF THE PREFERRED EMBODIMENTS

Figure 1A:
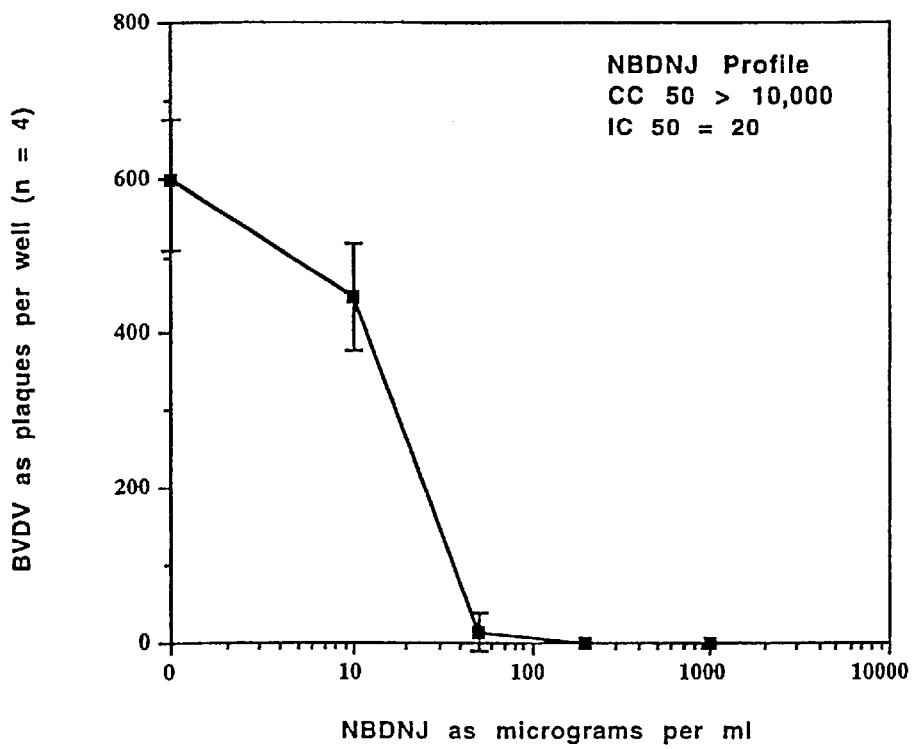
FIG. 1 shows the antiviral effect of DNJ derivatives N-butyl-DNJ (FIG. 1a) and N-nonyl-DNJ "578" (FIG. 1b) on Madin Darby Bovine Kidney (MDBK) cells infected with bovine viral diarrhea virus (BVDV).

Infections by viruses that require host cell glycosidase enzymes to synthesize and properly fold viral envelope glycoproteins can be treated by administering an inhibitor of those enzymes to the host cell. A target virus is any virus that acquires a component of its envelope in cooperation with internal cell membrane associated with the endoplasmic reticulum (ER). Preferred viruses are members of the flavivirus or pestivirus class.

By a "membrane associated with the ER" of a cell is meant a membrane which surrounds the lumen of the ER of the cell, a membrane which surrounds a lumen of the Golgi apparatus (GA), a membrane which surrounds the lumen of a vesicle passing from the ER to the GA, a membrane which surrounds the lumen of a vesicle passing from the GA to the ER, a membrane which surrounds the lumen of a vesicle passing from the GA or the ER to the plasma membrane of the cell, a membrane which surrounds the lumen of a vesicle passing from the GA or the ER to the nuclear membrane of the cell, or a membrane which surrounds the lumen of a vesicle passing from the GA or the ER to a mitochondrial membrane of the cell. It is contemplated that the methods of the invention are preferably applied to inhibiting the production of a virus that acquires any morphogenetic component by derivation from any of the internal membranes of the host cell.

By a "glucosidase enzyme associated with the ER" of a cell is meant a glucosidase enzyme which is embedded within, bound to the luminal side of, or contained within a membrane associated with, the ER of the cell. By way of example, mammalian α-glucosidase I and mammalian α-glucosidase II are glucosidase enzymes associated with the ER of a mammalian cell.

A virus-infected animal cell which is treated according to the methods of the invention may be any cell that comprises a glucosidase enzyme associated with an internal membrane of the cell, preferably an enzyme associated with the endoplasmic reticulum (ER). Treatment of mammalian cells, including but not limited to human liver cells and bovine monocytes are particularly preferred.

Agents that exhibit an inhibitory effect on glucosidases are believed to do so because they are structural analogs of glucose. One of these agents is the imino sugar designated 1,5-dideoxy-1,5-imino-D-glucitol (alternately designated deoxynojirimycin), hereinafter "DNJ." Numerous DNJ derivatives have been described. DNJ and its alkyl derivatives are potent inhibitors of the N-linked oligosaccharide processing enzymes, α-glucosidase I and α-glucosidase II (Saunier et al. (1982) J Biol Chem 257:14155–14161; Elbein (1987) Ann Rev Biochem 56:497–534). These glucosidases are associated with the endoplasmic reticulum of mammalian cells. The N-butyl and N-nonyl derivatives of DNJ may also inhibit glucosyltransferases associated with the Golgi.

Methods for treating a mammal infected with respiratory syncytial virus (RSV) using DNJ derivatives have been described (U.S. Pat. No. 5,622,972 issued to Bryant et al.). It is believed that DNJ exhibits its inhibitory effects on glucosidase because it is a glucose analog. However, Bryant discloses no mechanism by which DNJ derivatives exhibited the observed anti-RSV activity. RSV, a parnamyxovirus, acquires its envelope from the plasma membrane of an RSV-infected cell.

The use of DNJ and N-methyl-DNJ has also been disclosed to interrupt the replication of non-defective retroviruses such as human immunodeficiency virus (HIV), feline leukemia virus, equine infectious anemia virus, and lentiviruses of sheep and goats (U.S. Pat. Nos. 5,643,888 and 5,264,356; Acosta et al. (1994) Am J Hosp Pharm 51:2251–2267).

We have previously shown that human Hepatitis B virus (HBV) secretion from human hepatoblastoma cells in tissue culture is sensitive to inhibitors of the α-glucosidase activity in the endoplasmic reticulum (ER) under conditions that do not compromise host viability (Block et al. 1994). Hepatitis B virus (HBV) infected liver cells secrete infectious, nucleocapsid-containing virions as well as an excess of non-infectious "subviral" articles that do not contain DNA. All of these particles are believed to bud from an ER compartment or a post-ER compartment such as the intermediate compartment (Huovila et al. (1992) J Cell Biol 118:1305–1320; Patzer et al. (1986) J Virol 58:884–892). Inhibition of mature HBV egress is caused by inhibition of the activity of one or more of the glucosidase enzymes or glucosyltransferase enzymes normally associated with the endoplasmic reticulum (ER) of 2.15 cells, which are derived from HepG2 cells (Lu et al. (1995) Virology 213:660–665; Lu et al. (1997) Proc Natl Acad Sci USA 94:2380–2385).

Studies suggest that the anti-HIV properties of DNJ derivatives are the result of improper glycoprocessing of HIV envelope proteins, rather than direct inhibition of HIV budding from cells (Dedera et al. (1990) AIDS Res Hum Retr6vir 6:785–794; Fischer et al. (1995) J Virol 69:5791–5797; Taylor et al. (1994) Antimicrob Agents Chemother 38:1780–1787).

One derivative of DNJ, namely N-butyl-1,5-dideoxy-1,5-imino-D-glucitol (NBDNJ), prevents egress of the mature HBV virion from stable transfected HepG2 cells, but does not prevent egress of subviral particles (Block et al. (1994) Proc Natl Acad Sci USA 91:2235–2239). Thus, morphogenesis of HIV virions which are believed to bud through the plasma membrane, appears to be unaffected by the presence of NBDNJ. However, the infectivity of the virus particles released from HIV-infected cells exposed to NBDNJ is greatly reduced relative to HIV particles released from cells which were not exposed to NBDNJ (Dedera et al., supra Fisher et al., supra; Taylor et al., supra). These studies suggest that the anti-HIV properties of NBDNJ are the result of improper viral fusion of target cells, rather than direct irihibition of HIV budding from cells.

More recently we demonstrated the anti-viral effect of glucosidase inhibitors in a woodchuck animal model of HBV infection. In woodchucks chronically infected with woodchuck hepatitis virus (WHV), treatment with ER α-glucosidase inhibitors results in the disruption of the proper folding and transport of viral envelope glycoproteins and prevents the secretion of infectious enveloped virus (Block et al., 1998).

Most significantly and apparently different from the situation with HIV and RSV, inhibition of only modest amounts of glucosidase resulted in massive inhibition of HBV and BVDV secretion. This suggests that, unlike with HIV and RSV, etc., for viruses that bud from internal membranes, disruption of only a minority of envelope viral proteins is sufficient to inhibit secretion of the virus. This may be due to the fact that our evidence suggests that disrupted HBV and BVDV viral proteins act as "dominant negative" poisons of virus secretion and may themselves be considered the antiviral drug, as much as the drug itself.

ER α-glucosidases are responsible for the stepwise removal of terminal glucose residues from N-glycan chains attached to nascent glycoproteins. This enables the glycoproteins to interact with the ER chaperones calnexin and calreticulin, which bind exclusively to mono-glucosylated glyc proteins. Interaction with calnexin is crucial for the correct folding of some but not all glycoproteins, and inhibitors of the glucosidases can be used to specifically target proteins that depend on it. N-linked glycans play many roles in the fate and functions of glycoproteins. One function is to assist in the folding of proteins by mediating interactions of the lectin-like chaperone proteins calnexin and calreticulin with nascent glycoproteins. It is these interactions that can be prevented by inhibiting the activity of the α-glucosidases with agents such as N-butyl-DNJ and N-nonyl-DNJ, causing some proteins to be misfolded and retained within the endoplasmic reticulum (ER). We have shown that the N-nonyl-DNJ-induced misfolding of one of the hepatitis B virus (HBV) envelope glycoproteins prevents the formation and secretion of virus in vitro and that this inhibitor alters glycosylation and reduces the viral levels in an animal model of chronic HBV infection.

The exquisite sensitivity of HBV to alterations in the envelope proteins induced by α-glucosidase inhibition and the fact that it is not necessary to inhibit the enzyme to any great extent in order to achieve the observed anti-viral effect, led us to speculate that the sensitivity of the virus may be due to the fact that it has to oligomerize and assemble the envelope in the ER where folding takes place. Unlike the situation with HIV and RSV, a few misfolded envelope proteins may be sufficient to disrupt the proper envelopment process and amplify the adverse effect the inhibitor has on virus assembly as compared to the effect it has on host cell proteins, which do not seem to be impaired at anti-viral inhibitor concentrations. Our mechanism studies led us to propose that other viruses which acquire their envelopes from intracellular membranes such as the ER would be equally sensitive to ER α-glucosidase inhibition, provided one or more of their glycoproteins depended on calnexin-mediated folding.

Although HBV and HCV have completely different life cycles, they have three things in common: They target the liver, they bud from the ER and other internal membranes and their envelope, glycoprotein(s) fold via a calnexin-dependent pathway. This prompted us to investigate whether the same inhibitors shown to have an anti-viral effect on HBV could inhibit HCV by the same proposed mechanism.

The two HCV envelope glycoproteins E1 and E2, which contain five or six and eleven N-linked glycosylation sites, respectively, both interact with calnexin during productive folding (Choukhi et al., 1998). Due to the lack of an efficient cell culture replication system the understanding of HCV particle assembly is very, limited. However, the absence of complex glycans, the localization of expressed HCV glycoproteins in the ER, and the absence of these proteins on the cell surface suggest that initial virion morphogenesis occurs by budding into intracellular vesicles from the ER. Additionally, mature E1-E2 heterodimers do not leave the ER, and ER retention signals have been identified in the C-terminal regions of both E1 and E2.

Figure 1B:
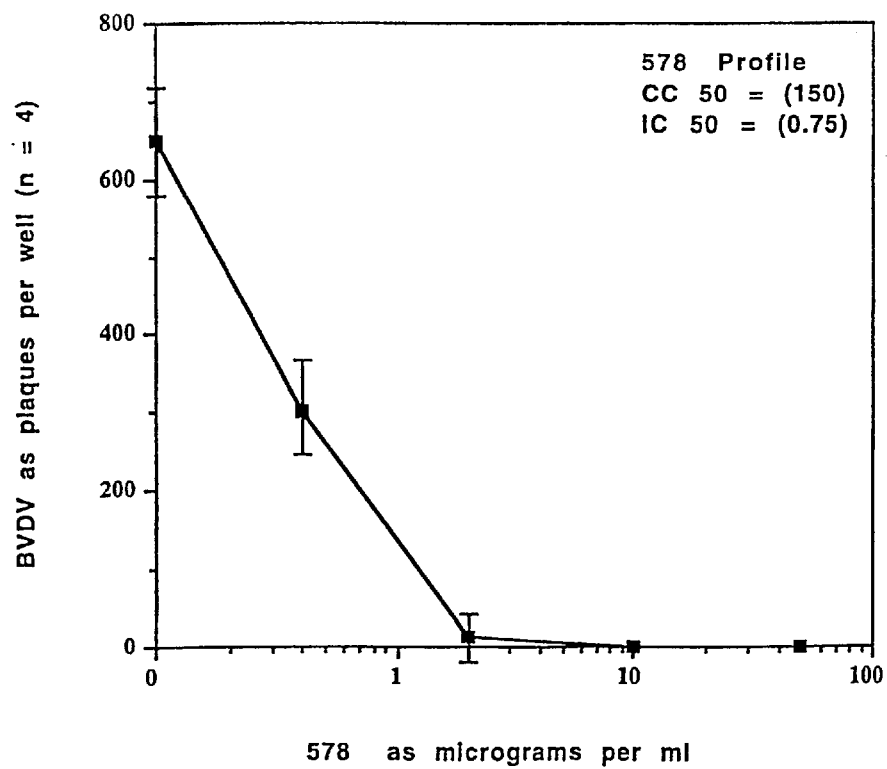

This led us to investigate the effect of glucosidase inhibitors on another ER-budding virus, bovine viral diarrhea virus (BVDV), the tissue culture surrogate of human hepatitis C virus (HCV). In the absence of a suitable cell culture system able to support replication of human HCV, bovine viral diarrhea virus (BVDV) serves as the FDA approved model organism for HCV (FIG. 1), as both share a significant degree of local protein region homology (Miller et al., 1990), common replication strategies, and probably the same sub-cellular location for viral envelopment. Compounds found to have an antiviral effect against BVDV are highly recommended as potential candidates for treatment of HCV.

BVDV, like HCV, is a small enveloped positive-stranded RNA virus and, like all viruses within the Flaviviridae, encodes all of its proteins in a single, long open reading frame (ORF), with the structural proteins in the N-terminal portion of the polyprotein and the non-structural or replicative proteins at the C-terminal end. The BVDV polyprotein has 6 potential N-glycosylation sites in the region encoding for the two heterodimer-forming envelope proteins gp25 (E1) and gp53 (E2), and 8 potential N-glycosylation sites in the region encoding for gp48 (EO), a hydrophilic secreted protein of unknown function. The structures of the oligosaccharides attached to any of these glycoproteins remain to be determined. BVDV proved to be even more sensitive to ER α-glucosidase inhibitors. This and the facts that the inhibitors used are preferentially taken up by liver-type cells in vitro and exhibit a prolonged retention in the liver in vivo give rise to the exciting possibility that glucosidase inhibitors could be used as broad based antiviral hepatitis agents.

Herein we describe the sensitivity of BVDV to glucosidase inhibition and discuss the possible reasons for ER-budding viruses being selectively dependent upon glycan processing. We have discovered that cytotoxicity resulting from exposure of mammalian cells in tissue culture to bovine viral diarrhea virus (BVDV) is prevented by addition of a glucosidase inhibitor to the tissue culture medium. The glucosidase inhibitors that were used in the examples below included a derivative of 1,5-dideoxy-1,5-imino-D-glucitol (DNJ), in particular, N-butyl-DNJ (NBDNJ). Moreover, inhibition of BVDV-induced cytotoxicity was achieved under conditions in which little, if any, toxicity toward host cells was observed to be mediated by NBDNJ. Because BVDV is an accepted tissue culture model of hepatitis C virus (HCV) (Henzler, H.-J. and K. Kaiser (1998) Nature Biotech 16:1077–1078), the compositions and methods described herein for inhibiting morphogenesis of BVDV are also useful for inhibiting morphogenesis of HCV.

The compositions effective in the practice of the methods of the invention comprise an animal glucosidase inhibitor, preferably a mammalian glucosidase inhibitor. Glucosidase inhibitors that are particularly contemplated in the methods of the invention are DNJ, 1,5-dideoxy-1,5-imino-D-glucitol, and derivatives thereof, having the formula $$\begin{array}{c}\text{structure with ring positions 1-6, substituents } R^3O, OR^4, OR^5, OR^6, \text{ and } N-R^1\end{array}$$

wherein
  $R^1$ is selected from the group consisting of
    (a) H;
    (b) alkyl;
    (c) alkenyl;
    (d) alkoxy;
    (e) acyl;
    (f) aryl;
    (g) aralkyl;
    (h) aroyl; and
    (i) aralkoxy; and
    (j) heterocyclic groups; and
  $R^3$, $R^4$, $R^5$ and $R^6$ are the same or different and are selected from the group consisting of
    H; acyl; and aroyl
wherein said alkyl and alkenyl groups have from 1 to 14 carbon atoms and are linear or branched, substituted or unsubstituted, and said alkenyl groups have from 1 to 6 double bonds; and wherein said aryl, aralkyl and aroyl groups have from 7 to 14 carbon atoms and heterocyclic groups are optionally substituted by halogen, hydroxy, $C_{1-10}$alkyl; $C_{1-10}$ alkylene; $C_{1-10}$acyl or $C_{1-10}$alkoxy; or an enantiomer or stereoisomer of said compound or a physiologically acceptable salt or solvate of said compound, enantiomer or stereoisomer.

Preferred are N-alkyl, N-acyl, N-aroyl, N-aralkyl, and O-acyl derivatives of DNJ. A derivative of DNJ, which is particularly preferred, is N-butyl-DNJ. Another preferred DNJ derivative is 1,5-dideoxy-1,5-nonylylimino-D-glucitol, which is herein designated N-nonyl-DNJ or NN-DNJ.

DNJ derivatives which have been described, for example in U.S. Pat. No. 5,622,972, include 1,5-dideoxy-1,5-butylimino-D-glucitol;
1,5-dideoxy-1,5-butylimino-4R,6-O-phenylmethylene-D-glucitol;
1,5-dideoxy-1,5-methylimino-D-glucitol;
1,5-dideoxy-1,5-hexylimino-D-glucitol;
1,5-dideoxy-1,5-nonylylimino-D-glucitol;
1,5-dideoxy-1,5-(2-ethylbutylimino)-D-glucitol;
1,5-dideoxy-1,5-benzyloxycarbonylimino-D-glucitol;
1,5-dideoxy-1,5-phenylacetylimino-D-glucitol;
1,5-dideoxy-1,5-benzoylimino-D-glucitol;
1,5-dideoxy-1,5-ethylmalonylimino-D-glucitol;
1,5-dideoxy-1,5-hydrocinnamoylimino-D-glucitol;
1,5-dideoxy-1,5-methylmalonylimino-D-glucitol;
1,5-dideoxy-1,5-butylimino-4R,6-O-phenylmethylene-D-glucitol;
1,5-dideoxy-1,5-phenoxymethyl)carbonylimino-D-glucitol;
1,5-dideoxy-1,5-ethylbutylimino-D-glucitol;
1,5-dideoxy-1,5-hexylimino-4R,6-O-phenylmethylene-D-glucitol;
1,5-dideoxy-1,5-(2-methylpentyl)imino-D-glucitol;
1,5-dideoxy-1,5-(3-nicotinoyl)imino-D-glucitol;
1,5-dideoxy-1,5-cinnamoylimino-D-glucitol;
1,5-dideoxy-1,5-(4-chlorophenyl)acetylimino-D-glucitol; and
1,5-dideoxy-1,5-(4-biphenyl)acetylimino-D-glucitol.

The compounds are used as the imino-protected species or the di- and tetra-acetates, propionates, butyrates, isobutyrates of the imino protected species.

Methods of synthesizing DNJ derivatives are known and are described, for example, in U.S. Pat. Nos. 5,622,972, 4,246,345, 4,266,025, 4,405,714, and 4,806,650, and U.S. patent application Ser. No. 07/851,818, filed Mar. 16, 1992.

Figure 7:
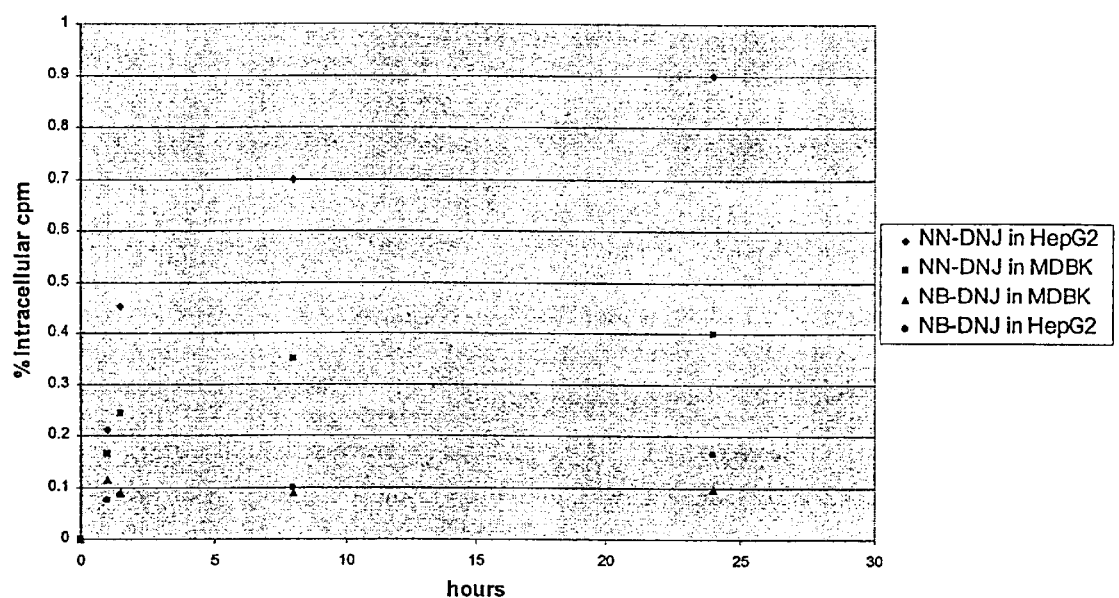
FIG. 7 shows the comparative uptake of radioactively labeled inhibitors by different cell types: ◆NN-DNJ in HepG2; ■NN-DNJ in MDBK; ▲NB-DNJ in MDBK; ●NB-DNJ in HepG2.
Figure 8:
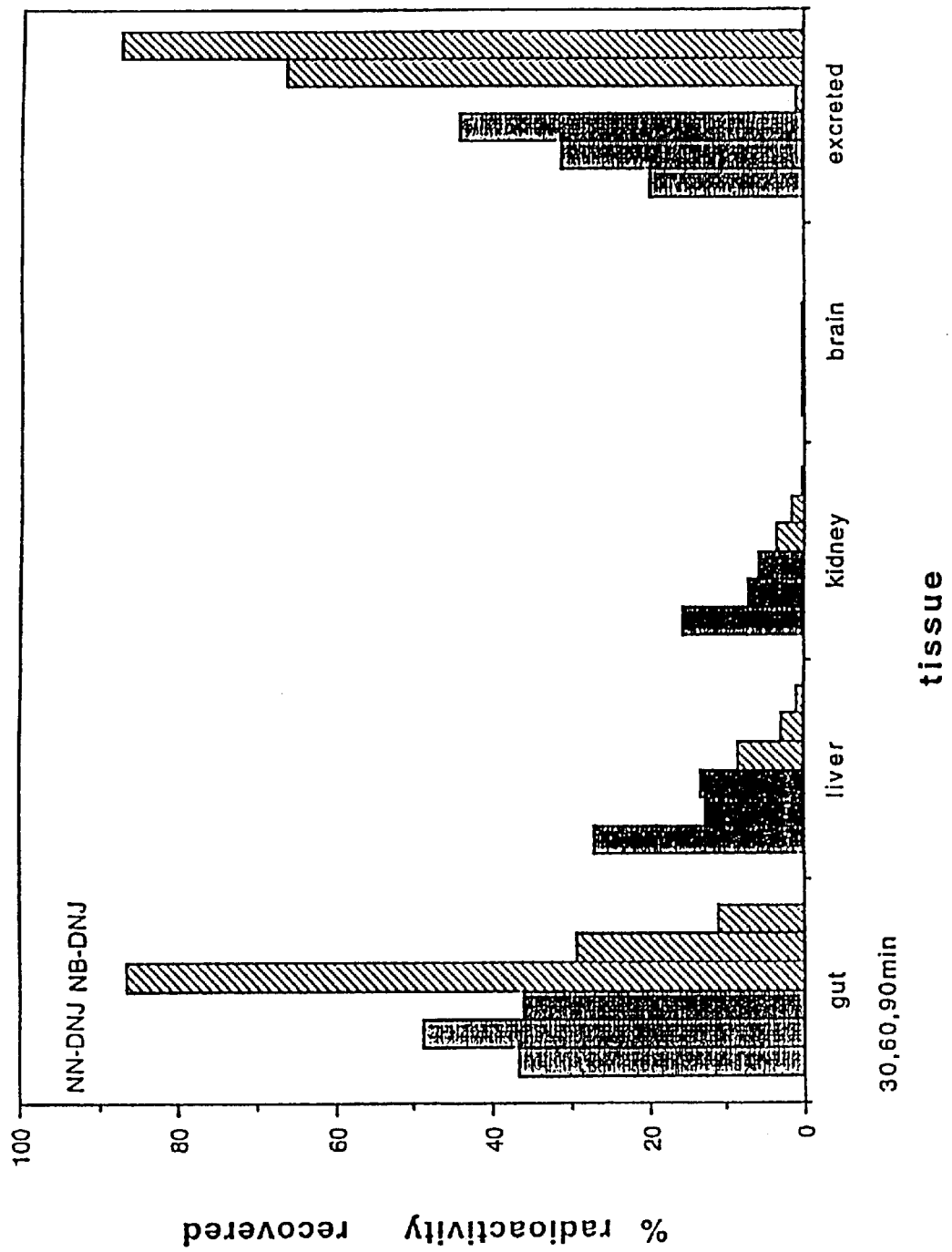
FIG. 8 shows the distribution of radiolabelled imino sugars N-nonyl-DNJ and N-butyl-DNJ in the organs of Balb C mice at 30, 60 and 90 min after administration. The Y axis value is the radioactivity associated with each organ as labeled along the X axis. The results are normalized according to organ weight.

The substituents on the basic 1,5-dideoxy-1,5-imino-D-glucitol can influence the potency of the compound as an antiviral agent and additionally can preferentially target the molecule to one organ rather than another. For example, the N-butyl-substituted DNJ is less potent than the N-nonyl-subsituted-DNJ in inhibiting the intracellular production of BVDV virus (FIG. 1 and Example 2). Methods for comparing the potencies of various substituted compounds are provided in Example 1. The N-nonyl-substituted DNJ is preferentially taken up by liver cells (FIG. 7 and Example 7). Methods for determining preferential targeting properties of variously substituted DNJs is provided in Example 8 and FIG. 8.

The DNJ derivatives described herein may be used in the free amine form or in a pharmaceutically acceptable salt form. Pharmaceutical salts and methods for preparing salt forms are provided in Berge, S. et al. (1977) J Pharm Sci 66(1):1–18. A salt form is illustrated, for example, by the HCl salt of a DNJ derivative. DNJ derivatives may also be used in the form of prodrugs such as the 6-phosphorylated derivatives described in U.S. Pat. Nos. 5,043,273 and 5,103,008. Use of compositions which further comprise a pharmaceutically acceptable carrier and compositions which further comprise components useful for delivering the composition to an animal are explicitly contemplated. Numerous pharmaceutically acceptable carriers useful for delivering the compositions to a human and components useful for delivering the composition to other animals such as cattle are known in the art. Addition of such carriers and components to the composition of the invention is well within the level of ordinary skill in the art.

The methods of the invention may further comprise use of a DNJ derivative and a supplemental antiviral compound. The supplemental antiviral compound may be any antiviral agent, which is presently recognized, or any antiviral agent which becomes recognized. By way of example, the supplemental antiviral compound may be interferon-alpha, ribavirin, lamivudine, brefeldin A, monensin, Tuvirumab™ (Protein Design Labs) Penciclovir™ (SmithKline Beecham, Philadelphia, Pa.), Famciclovir™ (SmithKline Beecham, Philadelphia, Pa.), Betaseron™ (Chiron Corp.), Theradigm-HBV™ (Cytel, La Jolla, Calif.), Adefovir Dipivoxil (GS 840, Gilead Sciences, Foster City, Calif.), Intron A™ (Schering Plough), Roferon™ (Roche Labs), beta interferon, BMS 200,475 (Bristol Myers Squibb), Lobucavir™ (Bristol Myers Squibb), FTC (Triangle, Inc.), DAPD (Triangle, Inc.), thymosin alpha peptide, Glycovir (Block et al. (1994) Proc Natl Acad Sci 91:2235–2240), granulocyte macrophage colony stimulating factor (Martin et al. (1993) Hepatology 18:775–780), an "immune-cytokine" (Guidotti et al. (1994) J Virol 68:1265–1270), CDG (Fourel et al. (1994) J Virol 68:1059–1065), or the like.

Treatment of Lipid Storage Diseases

Member of a group of lipidoses or lipid storage diseases in which glucosyl or galactosyl residues incorporated into complex lipids accumulate in the tissues can be treated using the glucosyltransferase inhibiting compounds of the invention, particularly N-nonyl-1,5-dideoxy-1,5-imino-D-glucitol according to the methods of the invention. Among these lipidoses are:

Gaucher's Disease

A familial autosomal recessive disorder of lipid metabolism resulting in an accumulation of abnormal glucocerebrosides in reticuloendothelial cells, and manifested clinically by hepatosplenomegaly, skin pigmentation, skeletal lesions and pingueculae.

The underlying defect in this disease is the lack of glucocerebrosidase activity, which normally hydrolyzes glucocerebroside to glucose and ceramide. The typical pathological finding is widespread reticulum cell hyperplasia. The cells are filled with glucocerebroside and a fibrillar cytoplasm, vary in shape and have one or several small eccentrically placed nuclei. These reticulum cells are found in the liver, spleen, lymph nodes and bone marrow.

Krabbe's Disease (Galactosylceramide Lipidosis)

A familial lipid storage disorder secondary to a deficiency of galactocerebroside β-galactosidase. A fatal infantile disorder characterized by progressive retardation, paralysis, blindness, deafness and pseudobulbar palsy.

Fabry's Disease (Galactosylgalactosylglucosyl Ceramide Lipidosis)

A familial disorder of lipid metabolism in which glycolipid accumulates in the many tissues. The metabolic disorder is caused by a deficiency of the lysosomal enzyme α-galactosidase as required for the metabolism of trihexosylceramide. Affected individuals have skin lesions and corneal opacities.

Tay-Sachs Disease: (GM2 Gangliosidosis)

A familial recessive disorder caused by deficiency of the enzyme hexosaminidase A, resulting in the accumulation of gangliosides (complex sphingolipids, comprising oligosaccharides made up of glucose and galactose) in the brain.

The amount of antiviral agent administered to an animal or to an animal cell according to the methods of the invention is an amount effective to inhibit the activity of a glucosidase enzyme associated with the ER or other internal membranes in the cell. The amount of glucosyltransferase inhibitor administered to an animal or an animal cell according to the methods of the invention is an amount sufficient to inhibit the activity of a glucosylotransferase enzyme associated with the ER or other internal membranes in the cell. The term "inhibit" as used herein refers to the detectable reduction and/or elimination of a biological activity exhibited in the absence of a DNJ derivative compound according to the invention. The term "effective amount" refers to that amount of composition necessary to achieve the indicated effect. The term "treatment" as used herein refers to reducing or alleviating symptoms in a subject, preventing symptoms from worsening or progressing, inhibition or elimination of the causative agent, or prevention of the infection or disorder in a subject who is free therefrom.

Thus, for example, treatment of a patient affected with lipidosis may be reduction of lipid accumulation in the affected cells, the prevention of progressive disease in a patient who has been treated. Treatment of viral infection includes destruction of the infecting agent, inhibition of or interference with its growth or maturation, neutralization of its pathological effects, and the like. The amount of the composition which is administered to the cell or animal is preferably an amount that does not induce any toxic effects which outweigh the advantages which accompany its administration.

Actual dosage levels of active ingredients in the pharmaceutical compositions of this invention may be varied so as to administer an amount of the active compound(s) that is effective to achieve the desired therapeutic response for a particular patient.

The selected dose level will depend on the activity of the selected compound, the route of administration, the severity of the condition being treated, and the condition and prior medical history of the patient being treated. However, it is within the skill of the art to start doses of the compound(s) at levels lower than required to achieve the desired therapeutic effect and to gradually increase the dosage until the desired effect is achieved. If desired, the effective daily dose may be divided into multiple doses for purposes of administration, for example, two to four doses per day. It will be understood, however, that the specific dose level for any particular patient will depend on a variety of factors, including the body weight, general health, diet, time and route of administration and combination with other drugs and the severity of the disease being treated. It is expected that the adult human daily dosage will normally range from between about one microgram to about one gram, preferably from between about 10 mg and 100 mg, of the glucosidase inhibitor per kilogram body weight. Of course, the amount of the composition which should be administered to a cell or animal is dependent upon numerous factors well understood by one of skill in the art, such as the molecular weight of the glucosidase inhibitor, the route of administration, and the like.

Pharmaceutical compositions that are useful in the methods of the invention may be administered systemically in oral solid formulations, ophthalmic, suppository, aerosol, topical or other similar formulations. In addition to the glucosidase- or lucosyltransferase-inhibitor, such pharmaceutical compositions may contain pharmaceutically-acceptable carriers and other ingredients known to enhance and facilitate drug administration. Other possible formulations, such as nanoparticles, liposomes, resealed erythrocytes, and immunologically based systems may also be used to administer the glucosidase- or glucosyltransferase-inhibitor according to the method of the invention. Such pharmaceutical compositions may be administered by any known route. The term "parenteral" used herein includes subcutaneous, intravenous, intraarterial, intrathecal, and injection and infusion techniques, without limitation. By way of example, the pharmaceutical compositions may be administered orally, topically, parenterally, systemically, or by a pulmonary route.

These compositions may be administered according to the methods of the invention in a single dose or in multiple doses which are administered at different times. Because the inhibitory effect of the composition upon a virus endures longer than the inhibitory effect of the composition upon normal host cell protein glucosylation, the dosing regimen may be adjusted such that virus propagation is retarded while host cell protein glucosylation is minimally effected. By way of example, an animal may be administered a dose of the composition of the invention once per week, whereby virus propagation is retarded for the entire week, while host cell protein glucosylation is inhibited only for a short period once per week.

One advantage of administering these compositions is that they inhibit an enzyme of the host, rather than a viral function. It is well known that viruses are capable of mutating, whereby a viral function which is susceptible to inhibition by an antiviral agent mutates such that it becomes resistant to inhibition by the agent in progeny viruses. By way of example, the ability of the HIV virus to mutate such that it is rendered impervious to a particular anti-viral agent such as. AZT is well documented. The methods of the invention have the advantage that the composition used in the methods targets a host cell function employed by a virus as a part of its life cycle. This host function, namely glucosylation catalyzed by a host gluosidase associated with the host cell's ER or glucosyl transfer catalyzed by a host glucosyltransferase associated with the host cell's ER, is not subject to alteration brought about by a mutation in the genome of the virus. Thus, strains of the virus which are resistant to inhibition by the composition of the invention are unlikely to develop.

Experimental Procedures

It was observed in the present invention that NBDNJ inhibited the ability of BVDV to form plaques on MDBK cell mnonolayers in tissue culture. By way of example, in two cultures which were exposed to BVDV but not to NBDNJ, there were 16 and 25 viral plaques in the wells containing the infected cells. Cells cultures which were exposed to BVDV and which were exposed to NBDNJ immediately after infection yielded no visible plaques, and the cell monolayers appeared healthy and viable, as assessed by neutral red staining.

Bovine viral diarrhea virus (BVDV) was used in these experiments as a surrogate for HCV. The use of a surrogate for HCV in tissue culture is necessary because HCV cannot be reliably propagated in tissue culture, nor in animals other than humans and chimpanzees. Like HCV, BVDV is a pestivirus that is believed to bud from the ER (Harasawa et al. (1995) Microb Immunol 39:979–985). BVDV is considered by virologists to be the closest biochemical surrogate of HCV for use in tissue culture (Suzich et al. (1993) J Virol 67:6152–6158; Donis (1995) Vet Clinics N Amer 11:393–423), and is recognized by leading experts, including informal statements from experts within the U.S. Food and Drug Administration, as an acceptable surrogate for HCV.

Apart from being useful as a surrogate for HCV, BVDV is also an important veterinary pathogen (Donis (1995) Vet Clinics N Amer 11 :393–423). BVDV infection is responsible for significant livestock loss in the USA (Sullivan et al. (1995) Virus Res 38:231–239).

The imino sugar derivatives N-butyl-deoxynojirimycin (NB-DNJ) and N-nonyl-deoxynojirimycin (NN-DNJ) strongly inhibit the cytopathic effect of BVDV on Madin Darby Bovine Kidney (MDBK) cells. Using plaque reduction and yield assays (Example 2), the nonyl compound (IC50=2.5 $\mu$M) was shown to be forty-six times more potent than the butyl compound (IC50=115 $\mu$M).

Figure 3:
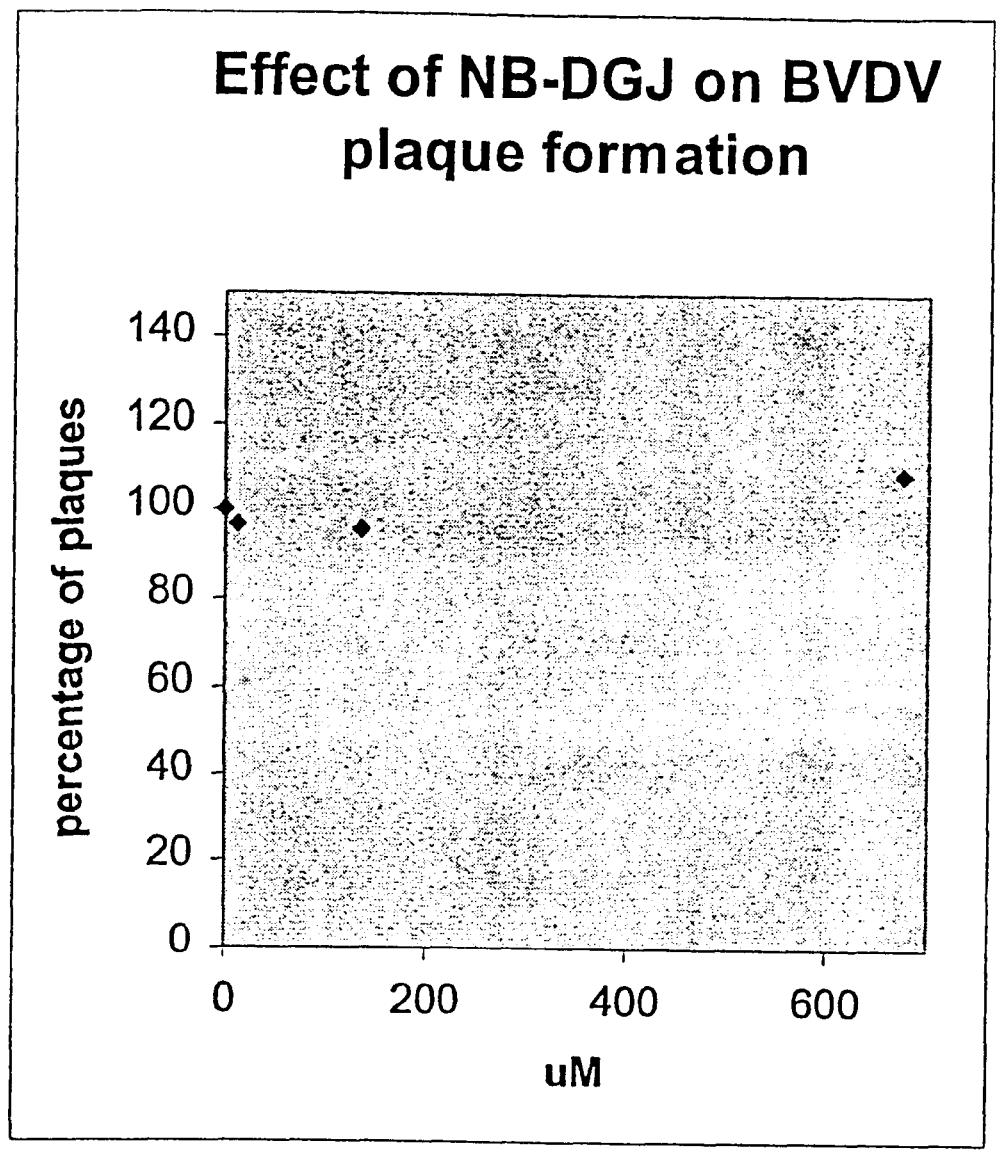
FIG. 3 shows the effect of N-butyl-DGJ (N-butyl-deoxygalactonojirimycin) on BVDV plaque formation, up to a concentration of 680 micrograms, at which the activity of ceramide-specific glucosyltransferase is completely inhibited. The Y axis scale represents the number of plaques observed in the treated systems as a percentage of the plaques resulting from infection with: an inhibitor-free supernate. The X axis scale represents the inhibitor concentrations used in the plaque assay.

To the extent that N-nonyl-DNJ is a much more potent inhibitor of glucosyltransferase activity in cell-based assays than is N-butyl-DNJ and inhibition of glucosyltransferase activity may be useful in treating many lysosomal glycolipid storage diseases (F. M. Platt, G. R. Neises, G. Reinkensmeier, M. J. Townsend, V. H. Perry, R. L. Proia, B. Winchester, R. A. Dwek, T. D. Butters (1997) Science 276:428–431), it is appreciated that nonyl DNJ and other alkyl chain derivatives of DNJ may be valuable in treating lysosomal glycolipid storage diseases such as Tay-Sachs, Gaucher's disease, Fabry's disease and the like. As both NB-DNJ and NN-DNJ compounds inhibit not only the ER $\alpha$-glucosidases, but also a ceramzide specific glucosyltransferase that is involved in glycosphingolipid biosynthesis, it was necessary to establish via which pathway these drugs exert their antiviral effect. The two pathways were pharmacologically dissected using N-butyl-deoxygalactonojirimycin (NB-DGJ), an inhibitor that targets only the glucosyltransferase. In the plaque reduction assay NB-DGJ had no effect on BVDV plaque formation (FIG. 3). The concentrations of NB-DGJ used were sufficient to completely inhibit the glucosyltransferase, as shown by the dose-dependent decrease of Glc-ceramide and gangliosides in $^{14}$C-palmitate-labelled NB-DGJ-treated MDBK cells (data not shown). This shows that the antiviral effect observed with NB-DNJ and NN-DNJ is due to the inhibition of the ER $\alpha$-glucosidases involved in N-glycan processing.

Figure 4:
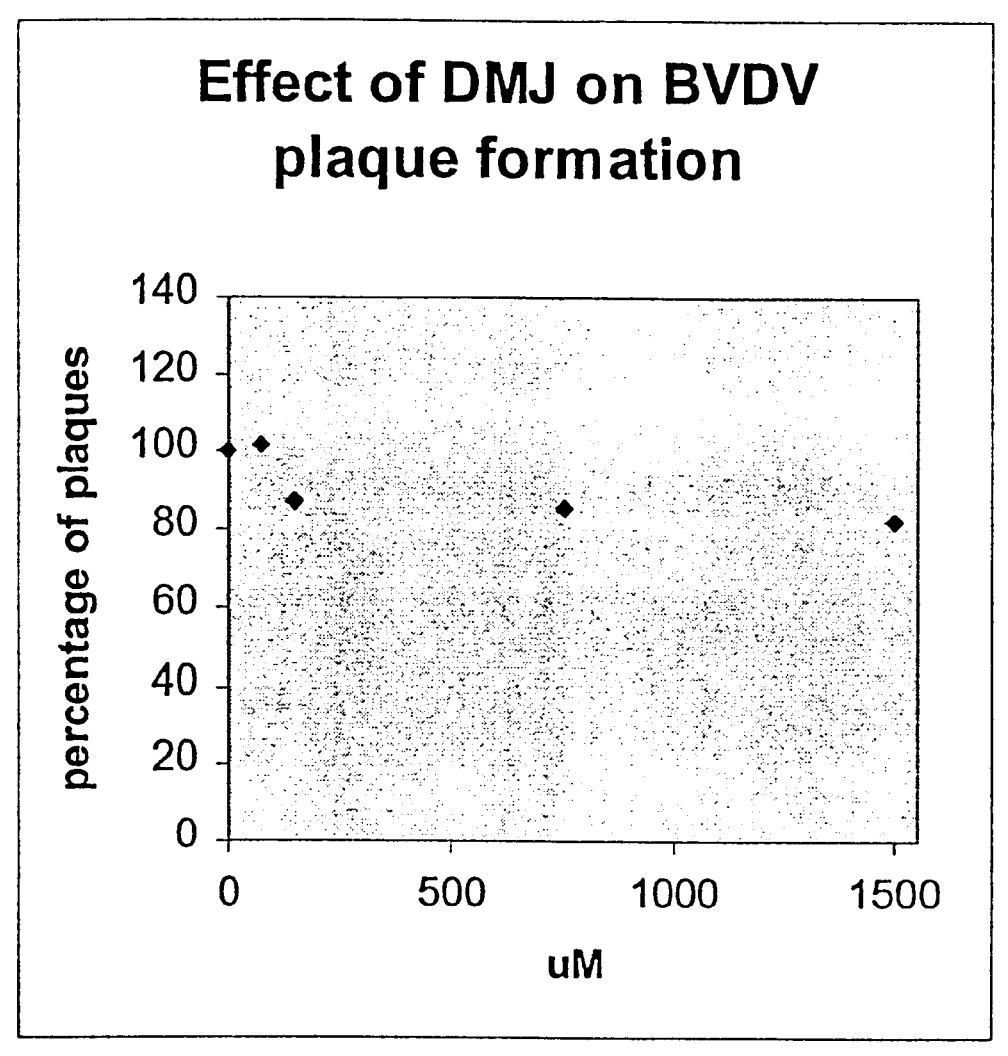

Golgi endo-$\alpha$-D-mannosidase, an enzyme which can provide an alternate pathway for achieving deglucosylation, thereby allowing even glucosidase-inhibited glycans to be further processed to complex-type oligosaccharides, has been shown to be present at substantial levels in MDBK cells. However, not all proteins can necessarily make use of this pathway. For example, the VSV-G protein remains endo-H-susceptible during a castanospermine imposed glucosidase blockade in MDBK cells. Therefore, treating MDBK cells with NB-DNJ and NNDNJ may also prevent the BVDV envelope glycoproteins from acquiring complex-type N-glycans, which may be crucial for viral secretion. To test this possibility the Golgi mannosidase I inhibitor deoxymannojirimycin (DMJ) was used in a plaque reduction assay (FIG. 4). DMJ, which prevents the formation of complex-type N-glycans without interfering with earlier steps in N-glycan biosynthesis had no effect on BVDV plaque formation. This means that the antiviral effect of NB-DNJ and NN-DNJ is mediated by a step prior to complex N-glycan formation.

As NB-DNJ targets a host cell enzyme, other N-glycosylated host proteins, including the viral receptor, may be functionally impaired. If that was the case the virus might be prevented from entering the host cell. To test this possibility, MDBK cells were grown in the absence or presence of 1 mg/ml of NB-DNJ for up to six days prior to infection with the virus. Pretreatment with the drug did not prevent viral entry (data not shown), showing that the viral receptor is, functional in glucosidase-inhibited cells.

In glucosidase-inhibited HepG2 cells infected with Hepatitis B virus (BBV), secretion of enveloped virus is prevented and viral DNA builds up within the cells. However, it is unclear whether the accumulated DNA is contained within infectious particles, as it is difficult to determine.the infectivity of HBV particles in tissue culture.

Figure 5:
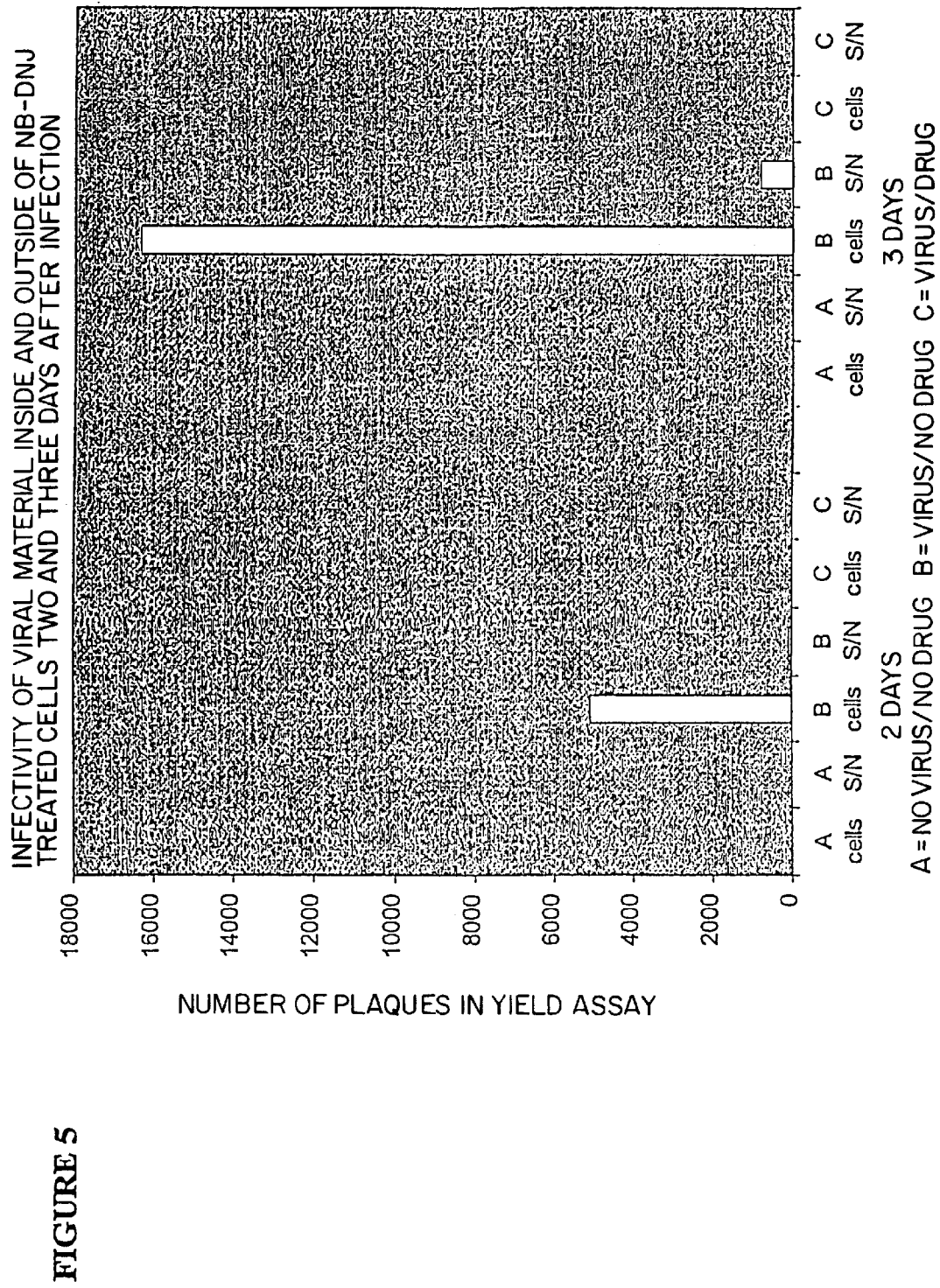
FIG. 5 shows the comparative infectivity of viral material within cells and in the cell culture supernates of (FIG. 5a) non-infected.

Prevention of BVDV secretion may also cause an accumulation of viral material inside the cells, and in this case it is easier to test whether this material is infectious. Infected untreated and NB-DNJ-treated cells were thoroughly washed and lysed by freeze-thawing after two and three days. Yield assays were performed to determine the number of plaque forming units (pfu) in the cell lysates as well as in the supernatants (FIG. 5). For untreated cells most of the infectious viral material (over 97%) was recovered from inside the cells after two days and after three days one-third of the infectious viral material could be detected in the supernatant. Significantly, NB-DNJ-treated cells contained no detectable infectious material after two days and very little infectious material after three days. No infectious material was found in the culture medium. These data show that BVDV does not accumulate inside inhibitor-treated cells in an infectious state.

Figure 6A:
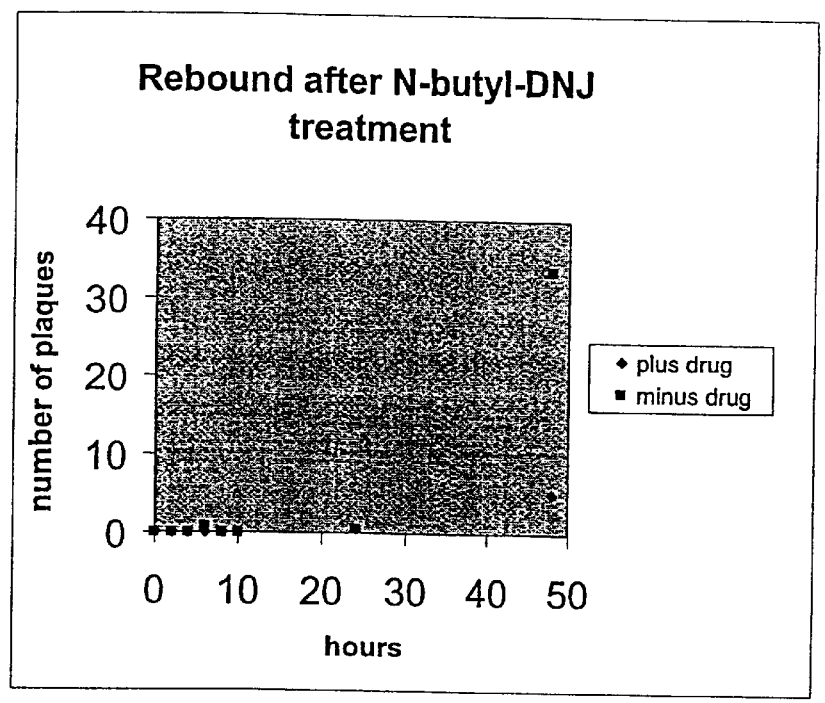
FIG. 6 shows the rebound of BVDV production in infected cells following withdrawal of treatment with N-butyl DNJ (FIG. 6a) and N-nonyl-DNJ (FIG. 6b): ◆=with drug; ■=drug withdrawn.
Figure 6B:
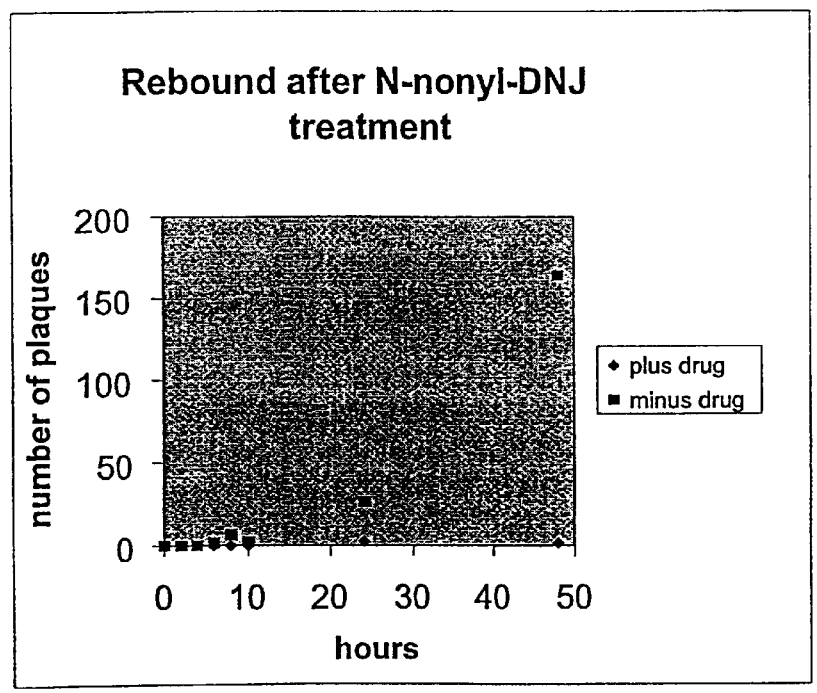

Cells infected with BVDV do not secrete or accumulate infectious virus as long as NB-DNJ is maintained in the culture medium and glucosidase is inhibited. We wanted to determine how long it would take the virus to recover from the effects of the glucosidase block and resume secretion after removal of inhibitor. Infected cells were treated with either 1 mg/ml NB-DNJ or 30 $\mu$g/ml NN-DNJ for two days (i.e., until plaques in untreated controls were fully developed), before the drug-containing medium was removed and replaced by drug-free (minus drug) or drug-containing (plus drug) medium. The medium was then removed at certain timepoints and assayed for infectious material using plaque reduction and yield assays. No infectious material was detected up to twenty-four hours after removal of the drug and the virus started to rebound only between the twenty-four and forty-eight hours time points (FIG. 6).

The imino sugars are reversible inhibitors of glucosidase and glucosyltransferase activity returns to near normal within 2 hours after drug removal. Yet the antiviral effect of N-nonyl-DNJ and N-butyl DNJ lasts long after 2 hours of removal (FIG. 6) and noted for HBV (Lu et al. (1997). It is therefore proposed that the antiviral effect of the imino sugar inhibitors is actually mediated by long-lived defective viral glycoproteins persisting in the cell long after drug removal. These long-lived defective glycoproteins act in a dominant negative fashion and may thus be considered the true antiviral agents themselves. The realization that the defective glycoproteins act as antiviral agents is inventive and will be useful in the treatment and development of new treatments for infections due to these viruses.

The invention is now described with reference to the following Examples. The examples are provided for the purpose of illustration only and the invention should in no way be construed as being limited thereby but rather should be construed to encompass any and all variations which become evident as a result of the teaching provided herein.

Experimental

Materials and Methods

Cells, Virus and Inhibitors. Non-cytopathic (ncp) BVDV-free MDBK cells and cytopathic (cp) BVDV virus (strain NADL) were kindly provided by Dr. John McCauley (Institute of Animal Health, Compton, UK). MDBK and HepG2 cells were maintained in RPMI 1640 medium (GEBCO/BRL) containing 10% fetal bovine serum (PAA Laboratories, Austria), which had been screened and found negative for the presence of BVDV and BVDV-specific antibodies. N-butyl-deoxynojirimycin (NBDNJ) and N-nonyl-deoxynojirimycin (NN-DNJ) were provided by Monsanto Searle. NB-DNJ was dissolved in medium and filtered just before use. NN-DNJ was made up as a 13 mg/ml stock solution in ethanol and diluted with medium prior to use. N-butyl-deoxygalactojifimycin (NB-DGJ) and deoxymannojirimycin (DMJ) were purchased from Boehringer Mannheim (Germany) and made up as 200 mM and 100 mM stock solutions in water, respectively. They were diluted with medium and filtered just before use. NB-[U-$^{14}$C] deoxynojirimycin (specific activity 4.4 mCi/mmol) and deoxynojirimycin (DNJ) were a gift of G. D. Searle.

In the absence of a suitable cell culture system able to support replication of human HCV, bovine viral diarrhea virus (BVDV) serves as the FDA approved model organism for HCV (FIG. 1), as both share a significant degree of local protein region homology (Miller et al., 1990), common replication strategies, and probably the same sub-cellular location for viral envelopment. Compounds found to have an antiviral effect against BVDV are highly recommended as potential candidates for treatment of HCV. Plaque Reduction and Yield Assays. MDBK cells were grown in six-well plates in the presence or absence of inhibitor (see Figure legends), infected with cp BVDV (moi=0.005; 500 pfu per well) for one hour at 37° C., The inoculum was then replaced with growth medium alone or with growth media and the antiviral agent and incubated for two or three days in the presence or absence of inhibitor (plaque reduction assay). After counting the plaques by eye under the microscope, the supernatant containing secreted infectious virus was removed from the wells and used to infect a fresh monolayer of MDBK cells in six-well plates. After three days the resulting plaques were counted under the microscope (yield assay).

EXAMPLE 1

Effect of the Presence of Antiviral Antiglucosidases on Plaque Formation in MDBK Cell Monolayers Exposed to BVDV MDBK cells (ATTC accession number 22 CCL F11859, BVDV-free) were grown to semi-confluence in individual wells of 24-well trays to form cell monolayers. The medium used was Dulbecco's modified Eagle's medium comprising 10% (v/v) horse serum. Approximately $10^5$ cells were infected with BVDV, NADL strain at a multiplicity of infection (moi) less than 1 ( plaque-forming conditions) by incubating the cells for one hour in the presence of an inoculum comprising a dilution of a virus stock solution comprising from approximately 500 to approximately 1,000 plaque forming units (PFU) per milliliter of the NADL strain of BVDV (ATCC accession number NADL 534VR) suspended in growth medium. The irioculum was then replaced with growth medium alone or with growth medium further comprising the amount of drug indicated on the axis of FIG. 5 (up to 1000 micrograms per milliliter NBDNJ). Three days post-infection, the cell monolayers were observed microscopically before and after staining with 0.2% (w/v) crystal violet in ethanol, and the presence and number of virus-induced plaques was determined (FIG. 5). Cells which were exposed to NBDNJ were viable, as determined by trypan dye exclusion and MTT assay (results reported as CC50, or the amount of drug required to cause a drop in viability on MTT activity of 50%). The results of these experiments are presented in the tables below and in FIG. 1.

TABLE 1

Treatment with N-butyl-DNJ. Cells which were exposed to NBDNJ were exposed to 1,000 micrograms per milliliter NBDNJ.

| Dilution of Virus | PFU Observed in Cells Not Exposed to NBDNJ | PFU Observed in Cells Exposed to NBDNJ |
| --- | --- | --- |
| $10^{-0}$ | C | ~100s, 100s |
| $10^{-1}$ | (100–1000), 400 | 0, 0 |
| $10^{-2}$ | 50, 45 | 0, 0 |
| $10^{-3}$ | 1?, 10 | 0, 0 |
| $10^{-4}$ | 0, 0 | 0, 0 |
| No Virus | 0, 0 | 0, 0 |

Note:
"C" indicates that confluent cell lysis was observed.
"I" indicates the presence of a small region of cell lysis which may represent a single PFU.
"s" indicates the presence of smaller plaques than those, which are normally, observed when a MDBK cell monolayer is infected with BVDV PFU.

EXAMPLE 2

Secretion of Infectious BVDV in the Presence of N-butyl-DNJ and N-nonyl-DNJ

MDBK cells were grown to semi-confluence in individual wells of 24-well trays. The cells were then infected by BVDV by incubating the cells for one hour at 37° C. in the presence of approximately 500 PFU of the NADL strain of BVDV suspended in growth medium. The inoculum was then replaced with growth medium alone or growth medium containing the concentration of NBDNJ or NNDNJ indicated in Table 2 and Table 3, respectively. After three days the supernatants were removed and used to infect fresh MDBK monolayers in six-well plates. After three days, the cell monolayers were observed microscopically before and after staining with 0.2% (w/v) crystal violet in ethanol for plaque counting, and 0.2% neutral red for viability and the presence and number of virus-induced plaques was determined. The results were expressed as percentages of the number of plaques resulting from infection with the inhibitor-free plaque assay supernatant (=100%). The results of these experiments are presented in Tables 2 and 3 and in the graphs depicted in FIG. 1A and FIG. 1B.

TABLE 2

Duplicate observations are separated by commas.

| Micrograms per milliliter NBDNJ added per well | 0 | 10 | 50 | 200 | 1000 | 1000 |
| --- | --- | --- | --- | --- | --- | --- |
| PFU added per well | ~500 | ~500 | ~500 | ~500 | ~500 | 0 |
| PFU observed per well | 500, C 500+, C | 200, 500+, 500+, 500+ | 10, 20, 20, 40 | 0, 0, 0, 0 | 0, 0, 0, 0 | 0, 0, 0, 0 |

Note: "C" indicates that confluent cell lysis was observed.

TABLE 3

Effect of the presence of N-nonyl-DNJ on Plaque Formation by BVDV.

| Micrograms per milliliter NNDNJ added per well | 0 | 0.4 | 2.0 | 10 | 50 | 50 |
|---|---|---|---|---|---|---|
| PFU added per well | ~500 | ~500 | ~500 | ~500 | ~500 | 0 |
| PFU observed per well | 200, 500+, 500+, C | 50, 100, 500, 200 | 100, 50, 50, 50 | 0, 0, 0, 0 | 0, 0, 0, 0 | 0, 0, 0, 0 |

Note: "C" indicates that confluent cell lysis was observed. N-nonyl-DNJ glucosidase inhibitor (Glycobiology Institute, Oxford University "Compound 578"). Duplicate observations are separated by commas.

The concentration of NB-DNJ which caused 50% inhibition of plaque formation ($IC_{50}$) was determined to be approximately 20 micrograms per milliliter. The concentration of NB-DNJ which induced death of 50% of MDBK cells ($CC_{50}$) was calculated to be greater than 1000 micrograms per milliliter. The value of $IC_{50}$ for N-nonyl-DNJ was approximately 0.75 micrograms per milliliter, and the value of $CC_{50}$ for N-nonyl-DNJ was approximately 100 micrograms per milliliter.

It is not clear whether the number or merely the size of virus-induced plaques was reduced by exposing the cells to NB-DNJ or NN-DNJ. There was no visible cytopathic effect in cells infected with BVDV and exposed to either 200 micrograms per milliliter NB-DNJ or 10 micrograms per milliliter NN-DNJ. Exposure of cells to 1000 micrograms per milliliter NB-DNJ did not result in measurable toxicity. Exposure of cells to 50 micrograms per milliliter NN-DNJ resulted in a monolayer in which cells had a "stressed" appearance, although no toxic effect could be quantified by vital staining.

The experimental results indicate that NN-DNJ. and NB-DNJ are highly effective anti-BVDV drugs. Because BVDV infection is the most relevant model of HCV infection available in tissue culture and because BVDV and HCV are biochemically, virologically, and genetically very similar, these data clearly indicate that NN-DNJ and NB-DNJ are also highly effective anti-HCV drugs.

EXAMPLE 3

Control Assay for the Inhibition of Ceramide-specific Glucosyltransferase by NB-DGJ MDBK cells were grown to confluency in $^{14}$C-palmitate N-butyl-deoxygalactonojirimycin (NB-DNJ). The cells were washed three times with PBS, scraped off the flasks and extracted using $CHCl_3$:MeOH (2:1, v/v) overnight at 4 degrees Centigrade. The first extract was kept and another 0.5 ml of $CHCl_3$:MeOH (2:1, v/v) was added for three hours at room temperature. The extracts were combined and aliquots scintillation-counted. Samples were adjusted to 200,000 cpm, dried under nitrogen, resuspended in 10 μl of $CHCl_3$: MeOH (2:1, v/v) and separated by TLC ($CHCl_3$: MeOH, 2:1, v/v). Radiolabeled lipids were detected by fluorography and the dose-dependent decrease of Glc-ceramide and gangliosides observed (data not shown) showed that the ceramide-specific glucosyltransferase was inhibited at concentrations which had no antiviral effect.

EXAMPLE 4

Control Assay for the Inhibition of Complex Sugar Formation by DMJ

MDBK cells were grown for three days in the absence/presence of 300 μg/ml DMJ. The cells were stained with Erythrina cristagalli (ECA) lectin (28 μg/ml and 280 μg/ml), which recognizes the GalβGalNAc epitope, and analysed by FACS. At the lower lectin concentration a shift in the staining intensity marked the decrease in binding sites (i.e. complex glycans) available for the lectin. At the higher lectin concentration, the presence of DMJ could protect cells from being killed by lectin binding. The results are shown graphically in FIG. 4.

EXAMPLE 5

Infectivity of Viral Material Inside and Outside of NB-DNJ-treated Cells After Infection Non-infected (A) and BVDV-infected (B and C) MDBK cells were grown in the absence (A and B) or presence (C) of 1 mg/ml of NB-DNJ for either two or three days. The supernatants were saved and the cells were washed and lysed by freeze-thawing. Yield assays were performed to determine the number of plaque-forming units (PFU) in the supernatants (S/N) and cell lysates. Results are plotted in FIG. 5.

EXAMPLE 6

Rebound of BVDV After Treatment of Infected Cells with NB-DNJ or NN-DNJ

Infected MDBK cells (500 pfu/well) were incubated in the presence of (A) 1 mg/ml N-butyl-DNJ or (B) 30 μg/ml N-nonyl-DNJ for two days. The drug-containing medium was removed and replaced by drug-free (minus drug) or drug-containing (plus drug) medium. The medium was removed at the indicated time points and assayed for infectious material in plaque reduction and yield assays. The results are shown in FIG. 6.

EXAMPLE 7

Uptake of Radioactively Labelled Inhibitors by Different Cell Types

MDBK and HepG2 cells were grown to confluency in 12-well plates and incubated in the presence of $C^{14}$-NB-DNJ and $H^3$-NN-DNJ (100000 cpm/well) for the times indicated. The supernatant was removed and kept. The cells were washed with PBS (2×500 μl), fixed with 500 μl of icecold 10% perchloric acid/2% phosphotungstic acid, washed twice with 500 μl of icecold ethanol and airdried. 500 μl of 0.5 M NaOH were used to lyse the cells overnight at room temperature. The percentage of radioactive counts in the supernatant, PBS wash and lysed cells was determined by liquid scintillation counting. The results are shown graphically in FIG. 7.

EXAMPLE 8

Preparation of N-[$^3$H]N-DNJ

DNJ (61 μmol) was reductively aminated with nonylaldehyde (1.2 mol equivalents) in the presence of one mol equivalent of sodium cyanoboro[³H]hydride (Amersham, 10 Ci/mmol) for 3 hours at room temperature. Tritium-labelled NN-DNJ was purified from the reaction mixture by cation-exchange and reverse-phase high performance liquid chromatography (HPLC). The product was greater than 95% radioactively pure by HPLC and the compound structure verified by mass spectrometry and ¹H-NMR. The specific activity was 145 mCi/mmol.

EXAMPLE 9

Organ Distribution of Radiolabelled Imino Sugars

Radiolabelled NN-DNJ and NB-DNJ were dried under vacuum, resuspended in whole mouse serum (Becton Dickenson) and sonicated on ice for one minute. The suspension was filtered using a 0.2 μm filter and the radioactivity was recovered in the filtrate with typical recovery rates of 78%–95%. The filtrates were administered to Balbc mice by oral gavage (1–3 μCi per mouse) and after 30, 60 and 90 minutes the mice were sacrificed by cervical dislocation and the organs removed. The organs were weighed and homogenized in water at 0.2–0.4 g/ml using an Ultra-Turrax homogenizer. Aliquots were taken for radioactivity determinations. The results are shown graphically in FIG. 8.

EXAMPLE 10

Treatment of Gaucher's Disease with N-nonyl-1,5-imino-D-glucitol

An individual affected with Gaucher's disease, diagnosed clinically by splenomegaly and typical reticulum cell hyperplasia with accumulation of abnormal glucocerebrosides in reticuloendothelial cells, is treated with N-nonyl-1,5-dideoxy-1,5-imino-D-glucitol (N-nonyl-DNJ) administered orally or parenterally. The dose is gradually increased from a base level of 10 mg/kg/day until a therapeutic response is observed, as indicated by improvement of clinical symptoms or a decrease of glucocerebrosides observed in reticuloendothelial cells on biopsy. Treatment with N-nonyl-DNJ is abated or reinstituted according to clinical response of the patient.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method for inhibiting production of a virus belonging to the Flaviviridae family comprising contacting a mammalian cell infected by said virus with an effective amount of a 1,5-dideoxy-1,5-imino-D-glucitol derivative compound having the general formula

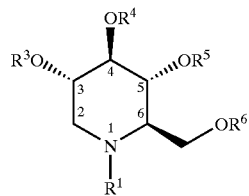

wherein $R^1$ is selected from the group consisting of
  H;
  alkyl;
  alkenyl;
  alkoxy;
  acyl;
  aryl;
  aralkyl;
  aroyl;
  aralkoxy; and
  heterocyclic groups; and $R^3$, $R^4$ and $R^5$ are the same or different and are selected from the group consisting of H; acyl; and aroyl groups; and $R^6$ is hydrogen, or an alkyl, alkenyl, acyl, aroyl or aralkyl group;

wherein said acyl, alkyl and alkenyl groups have from 1 to 14 carbon atoms and are linear or branched, substituted or unsubstituted, and said alkenyl groups have from 1 to 6 double bonds; and wherein said aryl groups and heterocyclic groups have from 7 to 14 carbon atoms and are optionally substituted by halogen, hydroxy, $C_{1-10}$alkyl; $C_{1-10}$alkylene; $C_{1-10}$acyl or $C_{1-10}$alkoxy; and enantiomers and stereoisomers of said compound and physiologically acceptable salts or solvates of said compound, enantiomer or stereoisomer.

2. A method according to claim 1 wherein the 1,5-dideoxy-1,5-imino-D-glucitol derivative compound is substituted at $R^1$ with an alkyl group; wherein said alkyl group has from 7 to 14 carbon atoms and is linear or branched, and substituted or unsubstituted.

3. A method according to claim 1 wherein the 1,5-dideoxy-1,5-imino-D-glucitol derivative compound is substituted at $R^1$ with an alkoxy group, wherein said alkoxy group has from 7 to 14 carbon atoms and is linear or branched, and substituted or unsubstituted.

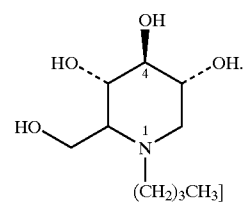

4. A method according to claim 1 wherein the 1,5-dideoxy-1,5-imino-D-glucitol derivative compound is substituted at $R^1$ with an alkyl, alkoxy, aralyl, aralkyl, or aralkoxy.

5. A method according to claim 1 wherein the 1,5-dideoxy-1,5-imino-D-glucitol derivative compound is substituted at $R^1$ with a nonyl group; wherein said nonyl group is linear or branched, and substituted or unsubstituted.

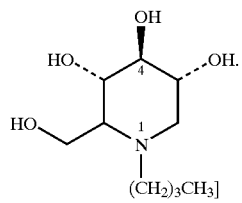

6. A method according to any one of claims 1–5 wherein the 1,5-dideoxy-1,5-imino-D-glucitol derivative compound is substituted at $R^3$, $R^4$, $R^5$ and $R^6$ by a hydrogen group.

7. A method according to any one of claims 2–6 wherein at least one of $R^3$, $R^4$ and $R^5$ is an acyl group.

8. A method according to claim 1 wherein the 1,5-dideoxy-1,5-imino-D-glucitol derivative compound, enantiomer, stereoisomer, or physiologically acceptable salt or solvate of said compound, enantiomer, or stereoisomer is administered to a mammal.

9. A method according to claim 8 wherein the 1,5-dideoxy-1,5-imino-D-gucitol derivative compound, enantiomer, stereoisomer, or physiologically acceptable salt or solvate of said compound, enantiomer, or stereoisomer is administered to a human.

10. A method according to claim 1 wherein the 1,5-dideoxy-1,5-imino-D-glucitol derivative compound, enantiomer, stereoisomer, or physiologically acceptable salt or solvate of said compound, enantiomer, or stereoisomer is administered to said mammalian cell in vivo.

11. A method according to claim 1 wherein said virus is a flavivirus.

12. A method according to claim 11 wherein the flavivirus is selected from the group consisting of yellow fever virus, dengue viruses 1–4, Japanese encephalitis virus, Murray Valley encephalitis, Rocio virus, West Nile fever virus, St. Louis encephalitis virus, tick-borne encephalitis virus, Louping ill virus, Powassan virus, Omsk hemorrhagic fever virus and Kyasanur forest disease virus.

13. A method according to claim 11 wherein the flavivirus is selected from the group consisting of yellow fever virus, a dengue virus and Japanese encephalitis virus.

14. A method according to claim 1 wherein said virus is a pestivirus.

15. A method for inhibiting production of a virus belonging to the Flaviviridae family comprising contacting a mammalian cell infected by said virus with an effective amount of a 1,5-dideoxy-1,5-imino-D-glucitol derivative compound having the general formula

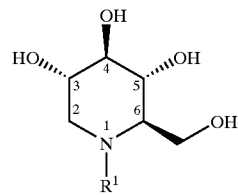

wherein $R^1$ is selected from the group consisting of H, alkyl, alkenyl, alkoxy, acyl, aryl, aralkyl, aroyl, aralkoxy, and heterocyclic groups; and
wherein said acyl, alkyl and alkenyl groups have from 7 to 14 carbon atoms and are linear or branched, substituted or unsubstituted; said alkenyl groups have from 1 to 6 double bonds; and said aryl groups and heterocyclic groups have from 7 to 14 carbon atoms and are optionally substituted by halogen, hydroxy, $C_{1-10}$alkyl; $C_{1-10}$ alkylene; $C_{1-10}$acyl or $C_{1-10}$alkoxy; and enantiomers and stereoisomers of said compound and physiologically acceptable salts or solvates of said compound, enantiomer or stereoisomer.

16. A method according to claim 15 wherein the 1,5-dideoxy-1,5-imino-D-glucitol derivative compound is substituted at $R^1$ with an alkyl group; wherein said alkyl group has from 7 to 14 carbon atoms and is linear or branched, and substituted or unsubstituted.

17. dA method according to claim 15 wherein the 1,5-dideoxy-1,5-imino-D-glucitol derivative compound is substituted at $R^1$ with an alkoxy group; wherein said alkoxy group has from 7 to 14 carbon atoms and is linear or branched, and substituted or unsubstituted.

18. A method according to claim 15 wherein the 1,5-dideoxy-1,5-imino-D-glucitol derivative compound is substituted at $R^1$ with an alkyl, alkoxy, aralkyl, or aralkoxy group.

19. A method according to claim 15 wherein the 1,5-dideoxy-1,5-imino-D-glucitol derivative compound is substituted at $R^1$ with a nonyl group; wherein said nonyl group is linear or branched, and substituted or unsubstituted.

20. A method according to claim 15 wherein the 1,5-dideoxy-1,5-imino-D-glucitol compound, enantiomer, stereoisomer, or physiologically acceptable salt or solvate of said compound, enantiomer, or stereoisomer is administered to a human in vivo.

21. A method according to claim 15 wherein said virus is a flavivirus.

22. A method according to claim 21 wherein the flavivirus is selected from the group consisting of yellow fever virus, dengue viruses 1–4, Japanese encephalitis virus, Murray Valley encephalitis, Rocio virus, West Nile fever virus, St. Louis encephalitis virus, tick-borne encephalitis virus, Louping ill virus, Powassan virus, Omsk hemorrhagic fever virus and Kyasanur forest disease virus.

23. A method according to claim 21 wherein the flavivirus is selected from the group consisting of yellow fever virus, a dengue virus and Japanese encephalitis virus.

24. A method according to claim 15 wherein said virus is a pestivirus.

25. A method for inhibiting production of a Hepatitis C virus comprising contacting a mammalian cell infected by said Hepatitis C virus with an effective amount of a 1,5-dideoxy-1,5-imino-D-glucitol derivative compound having the general formula

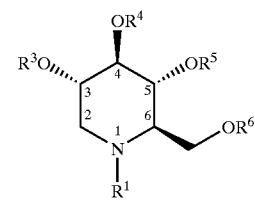

wherein
$R^1$ is selected from the group consisting of
H;
alkyl;
alkenyl;
alkoxy;
acyl;
aryl;
aralkyl;
aroyl;
aralkoxy; and
heterocyclic groups; and $R^3$, $R^4$ and $R^5$ are the same or different and are selected from the group consisting of H; acyl; and aroyl groups; and $R^6$ is hydrogen, or an alkyl, alkenyl, acyl, aroyl or aralkyl group;

wherein said acyl, alkyl and alkenyl groups have from 1 to 14 carbon atoms and are linear or branched, substituted or unsubstituted, and said alkenyl groups have from 1 to 6 double bonds; and wherein said aryl groups and heterocyclic groups have from 7 to 14 carbon atoms and are optionally substituted by halogen, hydroxy, $C_{1-10}$alkyl; $C_{1-10}$alkylene; $C_{1-10}$acyl or $C_{1-10}$alkoxy; and enantiomers and stereoisomers of said compound and physiologically acceptable salts or solvates of said compound, enantiomer or stereoisomer.

26. A method according to claim 25 wherein the 1,5-dideoxy-1,5-imino-D-glucitol derivative compound is substituted at $R^1$ with an alkyl group; wherein said alkyl group has from 7 to 14 carbon atoms and is linear or branched, and substituted or unsubstituted.

27. A method according to claim 25 wherein the 1,5-dideoxy-1,5-imino-D-glucitol derivative compound is substituted at $R^1$ with an alkoxy group; wherein said alkoxy group has from 7 to 14 carbon atoms and is linear or branched, and substituted or unsubstituted.

28. A method according to claim 25 wherein the 1,5-dideoxy-1,5-imino-D-glucitol derivative compound is substituted at $R^1$ with an alkyl, alkoxy, aralyl, aralkyl, or aralkoxy.

29. A method according to claim 25 wherein the 1,5-dideoxy-1,5-imino-D-glucitol derivative compound is substituted at $R^1$ with a nonyl group; wherein said nonyl group is linear or branched, and substituted or unsubstituted.

30. A method according to any one of claims 25–29 wherein the 1,5-dideoxy-1,5-imino-D-glucitol derivative compound is substituted at $R^3$, $R^4$, $R^5$ and $R^6$ by a hydrogen group.

31. A method according to any one of claims 25–29 wherein at least one of $R^3$, $R^4$ and $R^5$ is an acyl group.

32. A method according to claim 25 wherein the 1,5-dideoxy-1,5-imino-D-glucitol derivative compound, enantiomer, stereoisomer, or physiologically acceptable salt or solvate of said compound, enantiomer, or stereoisomer is administered to a human.

33. A method for inhibiting production of a Hepatitis C virus comprising contacting a mammalian cell infected by said Hepatitis C virus with an effective amount of a 1,5-dideoxy-1,5-imino-D-glucitol derivative compound having the general formula

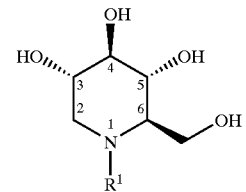

wherein $R^1$ is selected from the group consisting of H, alkyl, alkenyl, alkoxy, acyl, aryl, aralkyl, aroyl, aralkoxy, and heterocyclic groups; and wherein said acyl, alkyl and alkenyl groups have from 7 to 14 carbon atoms and are linear or branched, substituted or unsubstituted; said alkenyl groups have from 1 to 6 double bonds; and said aryl groups and heterocyclic groups have from 7 to 14 carbon atoms and are optionally substituted by halogen, hydroxy, $C_{1-10}$alkyl; $C_{1-10}$alkylene; $C_{1-10}$acyl or $C_{1-10}$alkoxy; and enantiomers and stereoisomers of said compound and physiologically acceptable salts or solvates of said compound, enantiomer or stereoisomer.

34. A method according to claim 33 wherein the 1,5-dideoxy-1,5-imino-D-glucitol derivative compound is substituted at $R^1$ with an alkyl group; wherein said alkyl group has from 7 to 14 carbon atoms and is linear or branched, and substituted or unsubstituted.

35. A method according to claim 33 wherein the 1,5-dideoxy-1,5-imino-D-glucitol derivative compound is substituted at $R^1$ with an alkoxy group; wherein said alkoxy group has from 7 to 14 carbon atoms and is linear or branched, and substituted or unsubstituted.

36. A method according to claim 33 wherein the 1,5-dideoxy-1,5-imino-D-glucitol derivative compound is substituted at $R^1$ with an alkyl, alkoxy, aralkyl, or aralkoxy group.

37. A method according to claim 33 wherein the 1,5-dideoxy-1,5-imino-D-glucitol derivative compound is substituted at $R^1$ with a nonyl group; wherein said nonyl group is linear or branched, and substituted or unsubstituted.

38. A method according to claim 33 wherein the 1,5-dideoxy-1,5-imino-D-glucitol compound, enantiomer, stereoisomer, or physiologically acceptable salt or solvate of said compound, enantiomer, or stereoisomer is administered to a human.

* * * * *